US009074001B2

(12) United States Patent
Dietrich et al.

(10) Patent No.: US 9,074,001 B2
(45) Date of Patent: Jul. 7, 2015

(54) TUBERCULOSIS TB VACCINE TO PREVENT REACTIVATION

(75) Inventors: Jes Dietrich, Copenhagen N (DK); Peter Andersen, Brønshøj (DK); Carina Vingsbo Lundberg, Höllviken (SE); Truc Thi Kim Than Hoang, Copenhagen S (DK)

(73) Assignee: STATENS SERUM INSTITUT (DK)

( * ) Notice: Subject to any disclaimer, the term of this patent is extended or adjusted under 35 U.S.C. 154(b) by 50 days.

(21) Appl. No.: 13/262,914

(22) PCT Filed: Apr. 23, 2010

(86) PCT No.: PCT/DK2010/000054
§ 371 (c)(1),
(2), (4) Date: Oct. 4, 2011

(87) PCT Pub. No.: WO2010/121618
PCT Pub. Date: Oct. 28, 2010

(65) Prior Publication Data
US 2012/0039925 A1    Feb. 16, 2012

(30) Foreign Application Priority Data
Apr. 24, 2009  (DK) .................. 2009 00539

(51) Int. Cl.
*A61K 39/04*      (2006.01)
*A61K 49/00*     (2006.01)
*A61K 39/00*      (2006.01)
*C07K 14/35*      (2006.01)

(52) U.S. Cl.
CPC .............. *C07K 14/35* (2013.01); *A61K 39/04* (2013.01); *A61K 2039/545* (2013.01)

(58) Field of Classification Search
USPC ............... 424/9.1, 9.2, 184.1, 185.1, 234.1, 424/248.1; 350/300, 350; 536/23.1, 23.7
See application file for complete search history.

(56) References Cited

U.S. PATENT DOCUMENTS

| 4,599,230 | A |   | 7/1986  | Milich et al. |
| 4,599,231 | A |   | 7/1986  | Milich et al. |
| 4,601,903 | A |   | 7/1986  | Frasch |
| 4,608,251 | A |   | 8/1986  | Mia |
| 5,955,077 | A | * | 9/1999  | Andersen et al. ......... 424/184.1 |
| 6,338,852 | B1 | * | 1/2002  | Reed et al. ............... 424/248.1 |
| 6,641,814 | B1 | * | 11/2003 | Andersen et al. ......... 424/190.1 |
| 2004/0057963 | A1 |   | 3/2004  | Andersen et al. |
| 2004/0115211 | A1 | * | 6/2004  | Andersen et al. ......... 424/184.1 |
| 2006/0040332 | A1 |   | 2/2006  | Macurer |
| 2008/0008724 | A1 | * | 1/2008  | Aagaard et al. ........... 424/204.1 |

FOREIGN PATENT DOCUMENTS

| JP | 2008-543890 | 12/2008 |
| WO | WO 96/40718 | 12/1996 |
| WO | WO 01/04151 A2 | 1/2001 |
| WO | WO 01/79274 A2 | 10/2001 |
| WO | WO 02/48391 A2 | 6/2002 |
| WO | WO 02/054072 | 7/2002 |
| WO | WO 2004/006952 A2 | 1/2004 |
| WO | WO 2006/072787 A1 | 7/2006 |
| WO | WO 2006/136162 A2 | 12/2006 |
| WO | WO 2008/000261 A2 | 1/2008 |

OTHER PUBLICATIONS

Anderson P. et al., "Vaccine strategies against latent tuberculosis infection" 2007, Trends Microbiol. 15(1), pp. 7-13.
Henao-Tamayo M. et al., "Post-exposure vaccination against *Mycobacterium tuberculosis*" Tuberculosis, Mar. 2009, vol. 89, No. 2, pp. 142-148.
Arend S. M. et al., "Antigenic Equivalence of Human T-Cell Responses to *Mycobacteria tuberculosis*-Specific RD1-Encoded Protein Antigens ESAT-6 and Culture Filtrate Protein 10 and to Mixtures of Synthetic Peptides" 2000, Infect. Immun. 68(8), pp. 3314-3321.
Brodin P. et al., "Dissection of ESAT-6 System 1 of *Mycobacterium tuberculosis* and Impact on Immunogenicity and Virulence" 2006, Infect. Immun. 74, pp. 88-98.
Cote-Sierra J. et al., "A new membrane-bound Oprl lipoprotein expression vector High production of heterologous fusion proteins in Gram (-) bacteria and the implications for oral vaccination" 1998, Gene Oct. 9, 221(1), pp. 25-34.
Doherty T. M. et al., "Immune Responses to the *Mycobacterium tuberculosis*-Specific Antigen ESAT-6 Signal Subclinical Infection among Contacts of Tuberculosis Patients" 2002, J Clin Microbiol. Feb. 40(2), pp. 704-706.
Gao L. Y. et al., "A mycobacterial virulence gene cluster extending RD1 is required for cytolysis, bacterial spreading and ESAT-6 secretion" 2004, Molecular Microbiology, pp. 1677-1693.
Gosselin E. et al., "Enhanced Antigen Presentation using Human Fcγ Receptor (Monocyte/Macrophage)-Specific Immunogens" 1992, J. Immunol. 149, pp. 3477-3481.
Guinn K. M. et al., "Individual RD1-region genes are required for export of ESAT-6/CFP-10 and for virulence of *Mycobacterium tuberculosis*" 2004, Mol. Microbiol. 51(2), pp. 359-370.
Harboe M. et al., "B-Cell Epitopes and Quantification of the ESAT-6 Protein of *Mycobacterium tuberculosis*" 1998, Infect. Immun. 66:2, pp. 717-723.
Hougardy J. M. et al., "Heparin-Binding-Hemagglutinin-Induced IFN-γ Release as a Diagnostic Tool for Latent Tuberculosis" 2007, PloS ONE, Oct. 3;2(10):e926.

(Continued)

*Primary Examiner* — Rodney P Swartz
(74) *Attorney, Agent, or Firm* — Knobbe, Martens, Olson & Bear, LLP

(57) ABSTRACT

The present invention discloses a vaccine or immunogenic composition that can be administered to latently infected individuals to prevent reactivation of latent tuberculosis infection caused by species of the tuberculosis complex microorganisms (*Mycobacterium tuberculosis, M. bovis, M. africanum*). The invention is base on a number of *M. tuberculosis* derived proteins and protein fragments which are constitutively expressed in different stages of the infection. The invention is directed to the use of these polypeptides, immunologically active fragments thereof and the genes encoding them for immunological compositions such as vaccines.

20 Claims, 7 Drawing Sheets

(56) References Cited

OTHER PUBLICATIONS

Figure 1:
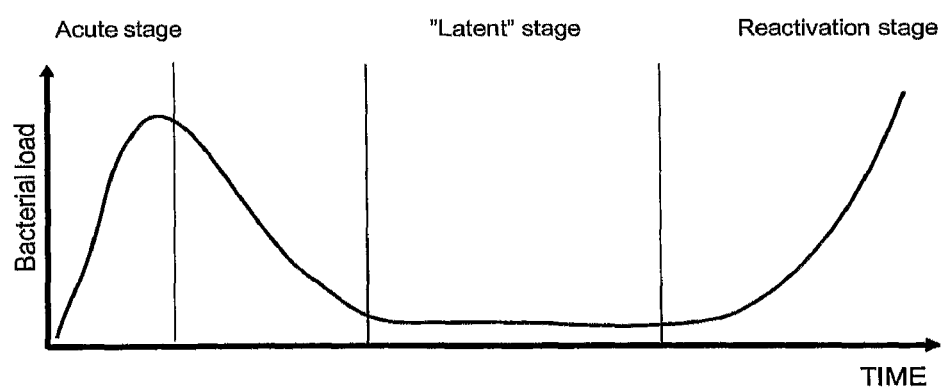

Kilgus J. et al., "Analysis of the Permissive, Association of a Malaria T Cell Epitope with DR Molecules" J. Immunol., Jan. 1, 1991, 146(1), pp. 307-315.
Leyten E. et al., "Human T-cell responses to 25 novel antigens encoded by genes of the dormancy regulon of *Mycobacterium tuberculosis*" Microbes and Infection, Elsevier, Paris, FR, vol. 8, No. 8, Jul. 2006, pp. 2052-2060.
Lin M. Y. et al., "Not to wake a sleeping giant: new insights into host-pathogen interactions identify new targets for vaccination against latent *Mycobacterium tuberculosis* infection" 2008, Biol. Chem. 389(5), pp. 497-511.
Lowrie D. B. et al., "Therapy of tuberculosis in mice by DNA vaccination" 1999, Nature, 400, pp. 269-271.
Lustig J.V. et al., "Humoral and Cellular Responses to Native Antigen following Oral and Parenteral Immunization with Lipid-Conjugated Bovine Serum Albumin" 1976, Cell Irnmunol. 24(1), pp. 164-172.
MacGurn J.A. et al , "A non-RD1 gene cluster is required for Snm secretion in *Mycobacterium tuberculosis*" 2005, 57(6), pp. 1653-1663.
Merrifield R.B. "Solid Phase Peptide Synthesis. I. The Synthesis of a Tetrapeptide" J. Am. Chem. Soc. 85(14), pp. 2149-2154.
Merrifield R.B. "Peptide Synthesis on a Solid Polyrner" Fed Proc. Am. Soc. Ex. Biol., 1962, p. 412, vol. 21.
Mowat A. M. et al., "Immune.stimulating complexes containing Quil A and protein antigen prime class I MHC-restricted T lymphocytes in vivo and are immunogenic by the oral route" 1991, Immunology 72(3), pp. 317-322.
Mustafa A. S. et al., "Multiple Epitopes from the *Mycobacterium tuberculosis* ESAT-6 Antigen are Recognized by Antigen-Specific Human T Cell Lines" 2000; Clin. Infect. Dis. 30 (suppl. 3), pp. 201-205.
Nagai S. et al., "Isolation and Partial Characterization of Major Protein Antigens in the Culture Fluid of *Mycobacterium tuberculosis*" 1991, Infect. Immun. 59:1, pp. 372-382.
Olsen A. W. et al., "Efficient protection against *Mycobacterium tuberculosis* by vaccination with a single subdominant epitope from the ESAT-6 antigen" Eur. J. Immunol. Jun. 2000, 30(6), pp. 1724-1732.
Pym A. S. et al., "Recombinant BCG exporting ESAT-6 confers enhanced protection against tuberculosis" May 2003:9(5), pp. 533-539.
Pearson W.R. et al., "Improved tools for biological sequence comparison" 1988, PNAS USA 85, pp. 2444-2448.
Raghaven S. et al., "Secreted transcription factor controls *Mycobacterium tuberculosis* virulence" 2008, Nature, 454, pp. 717-721.
Ravn P. et al., "Human T Cell Responses to the ESAT-6 Antigen from *Mycobacterium tuberculosis*" 1999, J. Infect. Dis. 179, pp. 637-645.
Rolph M.S. et al., "Recombinant viruses as vaccines and immunological tools" 1997, Curr. Opin. Immunol. 9, pp. 517-524.
Rogerson B.J. et al., "Expression levels at *Mycobacterium tuberculosis* antigen-encoding genes versus production levels of antigen-specfic T cells during stationary level lung infection in mice" 2006, Immunology, 118, pp. 195-201.

Rosenkrands I. et al., "Identification and Characterization of a 29-Kilodallon Protein from *Mycobacterium tuberculosis* Culture Filtrate Recognized by Mouse Memory Effector Cells" 1998, Infect. Immun. 66:6, pp. 2728-2735.
Ruhwald M. et al., "Improving T-Cell Assays for the Diagnosis of Latent TB Infection: Potential of a Diagnostic Test Based on IP-10" 2008, PloS ONE, Aug. 6;3(8):e2858.
Seder R.A. et al., "T-cell quality in memory and protection: implications for vaccine design" 2008, 8(4), pp. 247-258.
Sinigaglia F. et al., "A malaria T-cell epitope recognized in association with most mouse and human MHC class II molecules" Nature, Dec. 22-29, 1988, 336(6201), pp. 778-780.
Skjot R.L.V. et al., "Comparative Evaluation of Low-Molecular-Mass Proteins from *Mycobacterium tuberculosis* Identifies Members of the ESAT-6 Family as Immunodominant T-Cell Antigens" 2000, Infect. lmmun. 68:1, pp. 214-220.
Smith J. et al., "Evidence for Pore Formation in Host Cell Membranes by ESX-1-Secreted ESAT-6 and Its Role in *Mycobacterium marinum* Escape from the Vacuole" 2008, Infect. Immun. 76, pp. 5478-5487.
Stryhn A. et al., "Peptide binding specificity of major histocompatibility complex class I resolved into an array of apparently independent subspecificities: quantitation by peptide libraries and improved prediction of binding" 1996, Eur. J. Immunol. 26, pp. 1911-1918.
Talaat A.M. et al., "*Mycobacterial* Bacilli Are Metabolically Active during Chronic Tuberculosis in Marine Lungs: Insights from Genome-Wide Transcriptional Profiling" 2007, J. of Bact. 189, pp. 4265-4274.
Turner O.C. et al., "Lack of Protection in Mice and Necrotizing Bronchointerstitial Pneumonia with Bronchiolitis in Guinea Pigs Immunized with Vaccines Directed against the hsp60 Molecule of *Mycobacterium tuberculosis*" 2000, Infect. Immun. 68:6, pp. 3674-3679.
Thompson J. et al., "Cluster W: Improving the sensitivity of progressive multiple sequence alignment through sequence weighting, position-specfic gap penalties and weight matrix choice" Nucleic Acids Res. 1994, 22, pp. 4673-4680.
Ulmer Jeffrey B. et al., "Toward the development of DNA vaccines" Current Opinion in Biotechnology, 1996, pp. 653-658, vol. 7.
Ulmer Jeffrey B. et al., "DNA vaccines" Current Opinion in Biotechnology, 1996, pp. 531-536, vol. 8.
Van Pinxteren L.A. et al., "Control of latent *Mycobacterium tuberculosis* infection is dependent on CD8 T cells" 2000, Eur. J. Immunol. 30(12), pp. 3689-3698.
Stanley, S.A. et al., "Acute infection and macrophage subversion by *Mycobacterium tuberculosis* require a specialized secretion system", 2003, Proc Natl Acad. Sci. USA, vol. 100, No. pp. 2213001-2113006.
European Supplementary Search Report for EP 10 76 6664 dated Feb. 13, 2013.
Ganguly, Niladri et al., "Role of *M. tuberculosis* RD-1 region encoded secretory proteins in protective response and virulence" Tuberculosis, 2008, pp. 510-517, vol. 88.
Derrick, Steven C. et al., "The Safety of post-exposure vaccination of mice infected with *Mycobacterium tuberculosis*" Vaccine, 2008, pp. 6092-6098, vol. 26.
Zhang, Hai "Immune response and protective efficacy induced by fusion protein ESAT6-CFP10 of tuberculosis in mice" Chinese Journal of Cellular and Molecular Immunology , 2006, pp. 443-446, vol. 22, No. 4—XP-002691015.

* cited by examiner

SEQUENCE LISTING

```
<160> NUMBER OF SEQ ID NOS: 34

<210> SEQ ID NO 1
<211> LENGTH: 95
```

```
<212> TYPE: PRT
<213> ORGANISM: Mycobacterium tuberculosis

<400> SEQUENCE: 1

Met Thr Glu Gln Gln Trp Asn Phe Ala Gly Ile Glu Ala Ala Ser
1               5                   10                  15

Ala Ile Gln Gly Asn Val Thr Ser Ile His Ser Leu Leu Asp Glu Gly
                20                  25                  30

Lys Gln Ser Leu Thr Lys Leu Ala Ala Ala Trp Gly Gly Ser Gly Ser
                35                  40                  45

Glu Ala Tyr Gln Gly Val Gln Gln Lys Trp Asp Ala Thr Ala Thr Glu
        50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 2
<211> LENGTH: 100
<212> TYPE: PRT
<213> ORGANISM: Mycobacterium tuberculosis

<400> SEQUENCE: 2

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
                20                  25                  30

Glu Ser Thr Ala Gly Ser Leu Gln Gly Gln Trp Arg Gly Ala Ala Gly
                35                  40                  45

Thr Ala Ala Gln Ala Ala Val Val Arg Phe Gln Glu Ala Ala Asn Lys
        50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100

<210> SEQ ID NO 3
<211> LENGTH: 392
<212> TYPE: PRT
<213> ORGANISM: Mycobacterium tuberculosis

<400> SEQUENCE: 3

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
                20                  25                  30

Tyr Ser Ser Leu Glu Tyr Phe Glu Lys Ala Leu Glu Glu Leu Ala Ala
                35                  40                  45

Ala Phe Pro Gly Asp Gly Trp Leu Gly Ser Ala Ala Asp Lys Tyr Ala
        50                  55                  60

Gly Lys Asn Arg Asn His Val Asn Phe Phe Gln Glu Leu Ala Asp Leu
65                  70                  75                  80

Asp Arg Gln Leu Ile Ser Leu Ile His Asp Gln Ala Asn Ala Val Gln
                85                  90                  95

Thr Thr Arg Asp Ile Leu Glu Gly Ala Lys Lys Gly Leu Glu Phe Val
```

```
            100                 105                 110
Arg Pro Val Ala Val Asp Leu Thr Tyr Ile Pro Val Val Gly His Ala
        115                 120                 125

Leu Ser Ala Ala Phe Gln Ala Pro Phe Cys Ala Gly Ala Met Ala Val
    130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Thr
                    180                 185                 190

Leu Gly Glu Val Trp Glu Phe Ile Thr Asn Ala Leu Asn Gly Leu Lys
                195                 200                 205

Glu Leu Trp Asp Lys Leu Thr Gly Trp Val Thr Gly Leu Phe Ser Arg
    210                 215                 220

Gly Trp Ser Asn Leu Glu Ser Phe Phe Ala Gly Val Pro Gly Leu Thr
225                 230                 235                 240

Gly Ala Thr Ser Gly Leu Ser Gln Val Thr Gly Leu Phe Gly Ala Ala
                245                 250                 255

Gly Leu Ser Ala Ser Ser Gly Leu Ala His Ala Asp Ser Leu Ala Ser
                    260                 265                 270

Ser Ala Ser Leu Pro Ala Leu Ala Gly Ile Gly Gly Ser Gly Phe
                275                 280                 285

Gly Gly Leu Pro Ser Leu Ala Gln Val His Ala Ser Thr Arg Gln
    290                 295                 300

Ala Leu Arg Pro Arg Ala Asp Gly Pro Val Gly Ala Ala Glu Gln
305                 310                 315                 320

Val Gly Gly Gln Ser Gln Leu Val Ser Ala Gln Gly Ser Gln Gly Met
                325                 330                 335

Gly Gly Pro Val Gly Met Gly Gly Met His Pro Ser Ser Gly Ala Ser
                    340                 345                 350

Lys Gly Thr Thr Thr Lys Lys Tyr Ser Glu Gly Ala Ala Ala Gly Thr
                355                 360                 365

Glu Asp Ala Glu Arg Ala Pro Val Glu Ala Asp Ala Gly Gly Gly Gln
    370                 375                 380

Lys Val Leu Val Arg Asn Val Val
385                 390

<210> SEQ ID NO 4
<211> LENGTH: 184
<212> TYPE: PRT
<213> ORGANISM: Mycobacterium tuberculosis

<400> SEQUENCE: 4

Val Asp Leu Pro Gly Asn Asp Phe Asp Ser Asn Asp Phe Asp Ala Val
1               5                   10                  15

Asp Leu Trp Gly Ala Asp Gly Ala Glu Gly Trp Thr Ala Asp Pro Ile
                20                  25                  30

Ile Gly Val Gly Ser Ala Ala Thr Pro Asp Thr Gly Pro Asp Leu Asp
            35                  40                  45

Asn Ala His Gly Gln Ala Glu Thr Asp Thr Glu Gln Glu Ile Ala Leu
        50                  55                  60

Phe Thr Val Thr Asn Pro Pro Arg Thr Val Ser Val Ser Thr Leu Met
65                  70                  75                  80
```

```
Asp Gly Arg Ile Asp His Val Glu Leu Ser Ala Arg Val Ala Trp Met
                85                  90                  95

Ser Glu Ser Gln Leu Ala Ser Glu Ile Leu Val Ile Ala Asp Leu Ala
            100                 105                 110

Arg Gln Lys Ala Gln Ser Ala Gln Tyr Ala Phe Ile Leu Asp Arg Met
        115                 120                 125

Ser Gln Gln Val Asp Ala Asp Glu His Arg Val Ala Leu Leu Arg Lys
    130                 135                 140

Thr Val Gly Glu Thr Trp Gly Leu Pro Ser Pro Glu Glu Ala Ala Ala
145                 150                 155                 160

Ala Glu Ala Glu Val Phe Ala Thr Arg Tyr Ser Asp Asp Cys Pro Ala
                165                 170                 175

Pro Asp Asp Glu Ser Asp Pro Trp
            180

<210> SEQ ID NO 5
<211> LENGTH: 103
<212> TYPE: PRT
<213> ORGANISM: Mycobacterium tuberculosis

<400> SEQUENCE: 5

Met Thr Glu Asn Leu Thr Val Gln Pro Glu Arg Leu Gly Val Leu Ala
1               5                   10                  15

Ser His His Asp Asn Ala Ala Val Asp Ala Ser Ser Gly Val Glu Ala
            20                  25                  30

Ala Ala Gly Leu Gly Glu Ser Val Ala Ile Thr His Gly Pro Tyr Cys
        35                  40                  45

Ser Gln Phe Asn Asp Thr Leu Asn Val Tyr Leu Thr Ala His Asn Ala
    50                  55                  60

Leu Gly Ser Ser Leu His Thr Ala Gly Val Asp Leu Ala Lys Ser Leu
65                  70                  75                  80

Arg Ile Ala Ala Lys Ile Tyr Ser Glu Ala Asp Glu Ala Trp Arg Lys
                85                  90                  95

Ala Ile Asp Gly Leu Phe Thr
            100

<210> SEQ ID NO 6
<211> LENGTH: 132
<212> TYPE: PRT
<213> ORGANISM: Mycobacterium tuberculosis

<400> SEQUENCE: 6

Met Ser Thr Thr Phe Ala Ala Arg Leu Asn Arg Leu Phe Asp Thr Val
1               5                   10                  15

Tyr Pro Pro Gly Arg Gly Pro His Thr Ser Ala Glu Val Ile Ala Ala
            20                  25                  30

Leu Lys Ala Glu Gly Ile Thr Met Ser Ala Pro Tyr Leu Ser Gln Leu
        35                  40                  45

Arg Ser Gly Asn Arg Thr Asn Pro Ser Gly Ala Thr Met Ala Ala Leu
    50                  55                  60

Ala Asn Phe Phe Arg Ile Lys Ala Ala Tyr Phe Thr Asp Asp Glu Tyr
65                  70                  75                  80

Tyr Glu Lys Leu Asp Lys Glu Leu Gln Trp Leu Cys Thr Met Arg Asp
                85                  90                  95

Asp Gly Val Arg Arg Ile Ala Gln Arg Ala His Gly Leu Pro Ser Ala
            100                 105                 110
```

Ala Gln Gln Lys Val Leu Asp Arg Ile Asp Glu Leu Arg Arg Ala Glu
            115                 120                 125

Gly Ile Asp Ala
        130

<210> SEQ ID NO 7
<211> LENGTH: 573
<212> TYPE: PRT
<213> ORGANISM: Mycobacterium tuberculosis

<400> SEQUENCE: 7

Met Thr Asp Arg Leu Ala Ser Leu Phe Glu Ser Ala Val Ser Met Leu
1               5                   10                  15

Pro Met Ser Glu Ala Arg Ser Leu Asp Leu Phe Thr Glu Ile Thr Asn
            20                  25                  30

Tyr Asp Glu Ser Ala Cys Asp Ala Trp Ile Gly Arg Ile Arg Cys Gly
        35                  40                  45

Asp Thr Asp Arg Val Thr Leu Phe Arg Ala Trp Tyr Ser Arg Arg Asn
    50                  55                  60

Phe Gly Gln Leu Ser Gly Ser Val Gln Ile Ser Met Ser Thr Leu Asn
65                  70                  75                  80

Ala Arg Ile Ala Ile Gly Gly Leu Tyr Gly Asp Ile Thr Tyr Pro Val
                85                  90                  95

Thr Ser Pro Leu Ala Ile Thr Met Gly Phe Ala Ala Cys Glu Ala Ala
            100                 105                 110

Gln Gly Asn Tyr Ala Asp Ala Met Glu Ala Leu Glu Ala Ala Pro Val
        115                 120                 125

Ala Gly Ser Glu His Leu Val Ala Trp Met Lys Ala Val Val Tyr Gly
    130                 135                 140

Ala Ala Glu Arg Trp Thr Asp Val Ile Asp Gln Val Lys Ser Ala Gly
145                 150                 155                 160

Lys Trp Pro Asp Lys Phe Leu Ala Gly Ala Gly Val Ala His Gly
                165                 170                 175

Val Ala Ala Ala Asn Leu Ala Leu Phe Thr Glu Ala Glu Arg Arg Leu
            180                 185                 190

Thr Glu Ala Asn Asp Ser Pro Ala Gly Glu Ala Cys Ala Arg Ala Ile
        195                 200                 205

Ala Trp Tyr Leu Ala Met Ala Arg Arg Ser Gln Gly Asn Glu Ser Ala
    210                 215                 220

Ala Val Ala Leu Leu Glu Trp Leu Gln Thr Thr His Pro Glu Pro Lys
225                 230                 235                 240

Val Ala Ala Ala Leu Lys Asp Pro Ser Tyr Arg Leu Lys Thr Thr Thr
                245                 250                 255

Ala Glu Gln Ile Ala Ser Arg Ala Asp Pro Trp Asp Pro Gly Ser Val
            260                 265                 270

Val Thr Asp Asn Ser Gly Arg Glu Arg Leu Leu Ala Glu Ala Gln Ala
        275                 280                 285

Glu Leu Asp Arg Gln Ile Gly Leu Thr Arg Val Lys Asn Gln Ile Glu
    290                 295                 300

Arg Tyr Arg Ala Ala Thr Leu Met Ala Arg Val Arg Ala Lys Gly
305                 310                 315                 320

Met Lys Val Ala Gln Pro Ser Lys His Met Ile Phe Thr Gly Pro Pro
                325                 330                 335

Gly Thr Gly Lys Thr Thr Ile Ala Arg Val Val Ala Asn Ile Leu Ala
            340                 345                 350

```
Gly Leu Gly Val Ile Ala Glu Pro Lys Leu Val Glu Thr Ser Arg Lys
            355                 360                 365

Asp Phe Val Ala Glu Tyr Glu Gly Gln Ser Ala Val Lys Thr Ala Lys
        370                 375                 380

Thr Ile Asp Gln Ala Leu Gly Gly Val Leu Phe Ile Asp Glu Ala Tyr
385                 390                 395                 400

Ala Leu Val Gln Glu Arg Asp Gly Arg Thr Asp Pro Phe Gly Gln Glu
                405                 410                 415

Ala Leu Asp Thr Leu Leu Ala Arg Met Glu Asn Asp Arg Asp Arg Leu
                420                 425                 430

Val Val Ile Ile Ala Gly Tyr Ser Ser Asp Ile Asp Arg Leu Leu Glu
                435                 440                 445

Thr Asn Glu Gly Leu Arg Ser Arg Phe Ala Thr Arg Ile Glu Phe Asp
    450                 455                 460

Thr Tyr Ser Pro Glu Glu Leu Leu Glu Ile Ala Asn Val Ile Ala Ala
465                 470                 475                 480

Ala Asp Asp Ser Ala Leu Thr Ala Glu Ala Glu Asn Phe Leu Gln
                485                 490                 495

Ala Ala Lys Gln Leu Glu Gln Arg Met Leu Arg Gly Arg Arg Ala Leu
                500                 505                 510

Asp Val Ala Gly Asn Gly Arg Tyr Ala Arg Gln Leu Val Glu Ala Ser
                515                 520                 525

Glu Gln Cys Arg Asp Met Arg Leu Ala Gln Val Leu Asp Ile Asp Thr
    530                 535                 540

Leu Asp Glu Asp Arg Leu Arg Glu Ile Asn Gly Ser Asp Met Ala Glu
545                 550                 555                 560

Ala Ile Ala Ala Val His Ala His Leu Asn Met Arg Glu
                565                 570

<210> SEQ ID NO 8
<211> LENGTH: 480
<212> TYPE: PRT
<213> ORGANISM: Mycobacterium tuberculosis

<400> SEQUENCE: 8

Met Gly Leu Arg Leu Thr Thr Lys Val Gln Val Ser Gly Trp Arg Phe
1               5                   10                  15

Leu Leu Arg Arg Leu Glu His Ala Ile Val Arg Arg Asp Thr Arg Met
                20                  25                  30

Phe Asp Asp Pro Leu Gln Phe Tyr Ser Arg Ser Ile Ala Leu Gly Ile
            35                  40                  45

Val Val Ala Val Leu Ile Leu Ala Gly Ala Ala Leu Leu Ala Tyr Phe
        50                  55                  60

Lys Pro Gln Gly Lys Leu Gly Gly Thr Ser Leu Phe Thr Asp Arg Ala
65              70                  75                  80

Thr Asn Gln Leu Tyr Val Leu Leu Ser Gly Gln Leu His Pro Val Tyr
                85                  90                  95

Asn Leu Thr Ser Ala Arg Leu Val Leu Gly Asn Pro Ala Asn Pro Ala
                100                 105                 110

Thr Val Lys Ser Ser Glu Leu Ser Lys Leu Pro Met Gly Gln Thr Val
            115                 120                 125

Gly Ile Pro Gly Ala Pro Tyr Ala Thr Pro Val Ser Ala Gly Ser Thr
        130                 135                 140

Ser Ile Trp Thr Leu Cys Asp Thr Val Ala Arg Ala Asp Ser Thr Ser
```

```
            145                 150                 155                 160
        Pro Val Gln Thr Ala Val Ile Ala Met Pro Leu Glu Ile Asp Ala
                        165                 170                 175

Ser Ile Asp Pro Leu Gln Ser His Glu Ala Val Leu Val Ser Tyr Gln
                        180                 185                 190

Gly Glu Thr Trp Ile Val Thr Thr Lys Gly Arg His Ala Ile Asp Leu
                        195                 200                 205

Thr Asp Arg Ala Leu Thr Ser Ser Met Gly Ile Pro Val Thr Ala Arg
                        210                 215                 220

Pro Thr Pro Ile Ser Glu Gly Met Phe Asn Ala Leu Pro Asp Met Gly
        225                 230                 235                 240

Pro Trp Gln Leu Pro Pro Ile Pro Ala Ala Gly Ala Pro Asn Ser Leu
                        245                 250                 255

Gly Leu Pro Asp Asp Leu Val Ile Gly Ser Val Phe Gln Ile His Thr
                        260                 265                 270

Asp Lys Gly Pro Gln Tyr Tyr Val Val Leu Pro Asp Gly Ile Ala Gln
                        275                 280                 285

Val Asn Ala Thr Thr Ala Ala Ala Leu Arg Ala Thr Gln Ala His Gly
                        290                 295                 300

Leu Val Ala Pro Pro Ala Met Val Pro Ser Leu Val Val Arg Ile Ala
        305                 310                 315                 320

Glu Arg Val Tyr Pro Ser Pro Leu Pro Asp Glu Pro Leu Lys Ile Val
                        325                 330                 335

Ser Arg Pro Gln Asp Pro Ala Leu Cys Trp Ser Trp Gln Arg Ser Ala
                        340                 345                 350

Gly Asp Gln Ser Pro Gln Ser Thr Val Leu Ser Gly Arg His Leu Pro
                        355                 360                 365

Ile Ser Pro Ser Ala Met Asn Met Gly Ile Lys Gln Ile His Gly Thr
                        370                 375                 380

Ala Thr Val Tyr Leu Asp Gly Gly Lys Phe Val Ala Leu Gln Ser Pro
        385                 390                 395                 400

Asp Pro Arg Tyr Thr Glu Ser Met Tyr Tyr Ile Asp Pro Gln Gly Val
                        405                 410                 415

Arg Tyr Gly Val Pro Asn Ala Glu Thr Ala Lys Ser Leu Gly Leu Ser
                        420                 425                 430

Ser Pro Gln Asn Ala Pro Trp Glu Ile Val Arg Leu Leu Val Asp Gly
                        435                 440                 445

Pro Val Leu Ser Lys Asp Ala Ala Leu Leu Glu His Asp Thr Leu Pro
        450                 455                 460

Ala Asp Pro Ser Pro Arg Lys Val Pro Ala Gly Ala Ser Gly Ala Pro
        465                 470                 475                 480

<210> SEQ ID NO 9
<211> LENGTH: 747
<212> TYPE: PRT
<213> ORGANISM: Mycobacterium tuberculosis

<400> SEQUENCE: 9

Met Thr Thr Lys Lys Phe Thr Pro Thr Ile Thr Arg Gly Pro Arg Leu
        1               5                   10                  15

Thr Pro Gly Glu Ile Ser Leu Thr Pro Pro Asp Asp Leu Gly Ile Asp
                        20                  25                  30

Ile Pro Pro Ser Gly Val Gln Lys Ile Leu Pro Tyr Val Met Gly Gly
                        35                  40                  45
```

```
Ala Met Leu Gly Met Ile Ala Ile Met Val Ala Gly Gly Thr Arg Gln
    50              55                  60
Leu Ser Pro Tyr Met Leu Met Met Pro Leu Met Met Ile Val Met Met
65              70                  75                  80
Val Gly Gly Leu Ala Gly Ser Thr Gly Gly Gly Lys Lys Val Pro
                85                  90                  95
Glu Ile Asn Ala Asp Arg Lys Glu Tyr Leu Arg Tyr Leu Ala Gly Leu
                100                 105                 110
Arg Thr Arg Val Thr Ser Ser Ala Thr Ser Gln Val Ala Phe Phe Ser
            115                 120                 125
Tyr His Ala Pro His Pro Glu Asp Leu Leu Ser Ile Val Gly Thr Gln
        130                 135                 140
Arg Gln Trp Ser Arg Pro Ala Asn Ala Asp Phe Tyr Ala Ala Thr Arg
145                 150                 155                 160
Ile Gly Ile Gly Asp Gln Pro Ala Val Asp Arg Leu Leu Lys Pro Ala
                165                 170                 175
Val Gly Gly Glu Leu Ala Ala Ala Ser Ala Ala Pro Gln Pro Phe Leu
                180                 185                 190
Glu Pro Val Ser His Met Trp Val Val Lys Phe Leu Arg Thr His Gly
                195                 200                 205
Leu Ile His Asp Cys Pro Lys Leu Leu Gln Leu Arg Thr Phe Pro Thr
210                 215                 220
Ile Ala Ile Gly Gly Asp Leu Ala Gly Ala Ala Gly Leu Met Thr Ala
225                 230                 235                 240
Met Ile Cys His Leu Ala Val Phe His Pro Pro Asp Leu Leu Gln Ile
                245                 250                 255
Arg Val Leu Thr Glu Glu Pro Asp Asp Pro Asp Trp Ser Trp Leu Lys
                260                 265                 270
Trp Leu Pro His Val Gln His Gln Thr Glu Thr Asp Ala Ala Gly Ser
                275                 280                 285
Thr Arg Leu Ile Phe Thr Arg Gln Glu Gly Leu Ser Asp Leu Ala Ala
                290                 295                 300
Arg Gly Pro His Ala Pro Asp Ser Leu Pro Gly Gly Pro Tyr Val Val
305                 310                 315                 320
Val Val Asp Leu Thr Gly Gly Lys Ala Gly Phe Pro Pro Asp Gly Arg
                325                 330                 335
Ala Gly Val Thr Val Ile Thr Leu Gly Asn His Arg Gly Ser Ala Tyr
                340                 345                 350
Arg Ile Arg Val His Glu Asp Gly Thr Ala Asp Asp Arg Leu Pro Asn
                355                 360                 365
Gln Ser Phe Arg Gln Val Thr Ser Val Thr Asp Arg Met Ser Pro Gln
                370                 375                 380
Gln Ala Ser Arg Ile Ala Arg Lys Leu Ala Gly Trp Ser Ile Thr Gly
385                 390                 395                 400
Thr Ile Leu Asp Lys Thr Ser Arg Val Gln Lys Lys Val Ala Thr Asp
                405                 410                 415
Trp His Gln Leu Val Gly Ala Gln Ser Val Glu Glu Ile Thr Pro Ser
                420                 425                 430
Arg Trp Arg Met Tyr Thr Asp Thr Asp Arg Asp Arg Leu Lys Ile Pro
                435                 440                 445
Phe Gly His Glu Leu Lys Thr Gly Asn Val Met Tyr Leu Asp Ile Lys
                450                 455                 460
Glu Gly Ala Glu Phe Gly Ala Gly Pro His Gly Met Leu Ile Gly Thr
```

```
                465                 470                 475                 480
Thr Gly Ser Gly Lys Ser Glu Phe Leu Arg Thr Leu Ile Leu Ser Leu
                    485                 490                 495

Val Ala Met Thr His Pro Asp Gln Val Asn Leu Leu Thr Asp Phe
                500                 505                 510

Lys Gly Gly Ser Thr Phe Leu Gly Met Glu Lys Leu Pro His Thr Ala
                515                 520                 525

Ala Val Val Thr Asn Met Ala Glu Glu Ala Glu Leu Val Ser Arg Met
                530                 535                 540

Gly Glu Val Leu Thr Gly Glu Leu Asp Arg Arg Gln Ser Ile Leu Arg
545                 550                 555                 560

Gln Ala Gly Met Lys Val Gly Ala Ala Gly Ala Leu Ser Gly Val Ala
                    565                 570                 575

Glu Tyr Glu Lys Tyr Arg Glu Arg Gly Ala Asp Leu Pro Pro Leu Pro
                    580                 585                 590

Thr Leu Phe Val Val Asp Glu Phe Ala Glu Leu Leu Gln Ser His
                595                 600                 605

Pro Asp Phe Ile Gly Leu Phe Asp Arg Ile Cys Arg Val Gly Arg Ser
            610                 615                 620

Leu Arg Val His Leu Leu Ala Thr Gln Ser Leu Gln Thr Gly Gly
625                 630                 635                 640

Val Arg Ile Asp Lys Leu Glu Pro Asn Leu Thr Tyr Arg Ile Ala Leu
                    645                 650                 655

Arg Thr Thr Ser Ser His Glu Ser Lys Ala Val Ile Gly Thr Pro Glu
                660                 665                 670

Ala Gln Tyr Ile Thr Asn Lys Glu Ser Gly Val Gly Phe Leu Arg Val
                675                 680                 685

Gly Met Glu Asp Pro Val Lys Phe Ser Thr Phe Tyr Ile Ser Gly Pro
                690                 695                 700

Tyr Met Pro Pro Ala Ala Gly Val Glu Thr Asn Gly Glu Ala Gly Gly
705                 710                 715                 720

Pro Gly Gln Gln Thr Thr Arg Gln Ala Ala Arg Ile His Arg Phe Thr
                    725                 730                 735

Ala Ala Pro Val Leu Glu Glu Ala Pro Thr Pro
                740                 745

<210> SEQ ID NO 10
<211> LENGTH: 591
<212> TYPE: PRT
<213> ORGANISM: Mycobacterium tuberculosis

<400> SEQUENCE: 10

Met Thr Ala Glu Pro Glu Val Arg Thr Leu Arg Glu Val Val Leu Asp
1               5                   10                  15

Gln Leu Gly Thr Ala Glu Ser Arg Ala Tyr Lys Met Trp Leu Pro Pro
                20                  25                  30

Leu Thr Asn Pro Val Pro Leu Asn Glu Leu Ile Ala Arg Asp Arg Arg
            35                  40                  45

Gln Pro Leu Arg Phe Ala Leu Gly Ile Met Asp Glu Pro Arg Arg His
        50                  55                  60

Leu Gln Asp Val Trp Gly Val Asp Val Ser Gly Ala Gly Gly Asn Ile
65                  70                  75                  80

Gly Ile Gly Gly Ala Pro Gln Thr Gly Lys Ser Thr Leu Leu Gln Thr
                85                  90                  95
```

-continued

```
Met Val Met Ser Ala Ala Ala Thr His Ser Pro Arg Asn Val Gln Phe
             100                 105                 110

Tyr Cys Ile Asp Leu Gly Gly Gly Leu Ile Tyr Leu Glu Asn Leu
        115                 120                 125

Pro His Val Gly Gly Val Ala Asn Arg Ser Glu Pro Asp Lys Val Asn
        130                 135                 140

Arg Val Val Ala Glu Met Gln Ala Val Met Arg Gln Arg Glu Thr Thr
145                 150                 155                 160

Phe Lys Glu His Arg Val Gly Ser Ile Gly Met Tyr Arg Gln Leu Arg
                165                 170                 175

Asp Asp Pro Ser Gln Pro Val Ala Ser Asp Pro Tyr Gly Asp Val Phe
            180                 185                 190

Leu Ile Ile Asp Gly Trp Pro Gly Phe Val Gly Glu Phe Pro Asp Leu
        195                 200                 205

Glu Gly Gln Val Gln Asp Leu Ala Ala Gln Gly Leu Ala Phe Gly Val
        210                 215                 220

His Val Ile Ile Ser Thr Pro Arg Trp Thr Glu Leu Lys Ser Arg Val
225                 230                 235                 240

Arg Asp Tyr Leu Gly Thr Lys Ile Glu Phe Arg Leu Gly Asp Val Asn
                245                 250                 255

Glu Thr Gln Ile Asp Arg Ile Thr Arg Glu Ile Pro Ala Asn Arg Pro
            260                 265                 270

Gly Arg Ala Val Ser Met Glu Lys His His Leu Met Ile Gly Val Pro
        275                 280                 285

Arg Phe Asp Gly Val His Ser Ala Asp Asn Leu Val Glu Ala Ile Thr
        290                 295                 300

Ala Gly Val Thr Gln Ile Ala Ser Gln His Thr Glu Gln Ala Pro Pro
305                 310                 315                 320

Val Arg Val Leu Pro Glu Arg Ile His Leu His Glu Leu Asp Pro Asn
                325                 330                 335

Pro Pro Gly Pro Glu Ser Asp Tyr Arg Thr Arg Trp Glu Ile Pro Ile
            340                 345                 350

Gly Leu Arg Glu Thr Asp Leu Thr Pro Ala His Cys His Met His Thr
        355                 360                 365

Asn Pro His Leu Leu Ile Phe Gly Ala Ala Lys Ser Gly Lys Thr Thr
        370                 375                 380

Ile Ala His Ala Ile Ala Arg Ala Ile Cys Ala Arg Asn Ser Pro Gln
385                 390                 395                 400

Gln Val Arg Phe Met Leu Ala Asp Tyr Arg Ser Gly Leu Leu Asp Ala
                405                 410                 415

Val Pro Asp Thr His Leu Leu Gly Ala Gly Ala Ile Asn Arg Asn Ser
            420                 425                 430

Ala Ser Leu Asp Glu Ala Val Gln Ala Leu Ala Val Asn Leu Lys Lys
        435                 440                 445

Arg Leu Pro Pro Thr Asp Leu Thr Ala Gln Leu Arg Ser Arg Ser
        450                 455                 460

Trp Trp Ser Gly Phe Asp Val Val Leu Leu Val Asp Asp Trp His Met
465                 470                 475                 480

Ile Val Gly Ala Ala Gly Gly Met Pro Pro Met Ala Pro Leu Ala Pro
                485                 490                 495

Leu Leu Pro Ala Ala Ala Asp Ile Gly Leu His Ile Ile Val Thr Cys
            500                 505                 510

Gln Met Ser Gln Ala Tyr Lys Ala Thr Met Asp Lys Phe Val Gly Ala
```

```
                515                 520                 525
Ala Phe Gly Ser Gly Ala Pro Thr Met Phe Leu Ser Gly Glu Lys Gln
        530                 535                 540
Glu Phe Pro Ser Ser Glu Phe Lys Val Lys Arg Arg Pro Pro Gly Gln
545                 550                 555                 560
Ala Phe Leu Val Ser Pro Asp Gly Lys Glu Val Ile Gln Ala Pro Tyr
                565                 570                 575
Ile Glu Pro Pro Glu Glu Val Phe Ala Ala Pro Pro Ser Ala Gly
        580                 585                 590

<210> SEQ ID NO 11
<211> LENGTH: 99
<212> TYPE: PRT
<213> ORGANISM: Mycobacterium tuberculosis

<400> SEQUENCE: 11

Met Glu Lys Met Ser His Asp Pro Ile Ala Ala Asp Ile Gly Thr Gln
1               5                   10                  15
Val Ser Asp Asn Ala Leu His Gly Val Thr Ala Gly Ser Thr Ala Leu
                20                  25                  30
Thr Ser Val Thr Gly Leu Val Pro Ala Gly Ala Asp Glu Val Ser Ala
            35                  40                  45
Gln Ala Ala Thr Ala Phe Thr Ser Glu Gly Ile Gln Leu Leu Ala Ser
        50                  55                  60
Asn Ala Ser Ala Gln Asp Gln Leu His Arg Ala Gly Glu Ala Val Gln
65                  70                  75                  80
Asp Val Ala Arg Thr Tyr Ser Gln Ile Asp Asp Gly Ala Ala Gly Val
                85                  90                  95
Phe Ala Glu

<210> SEQ ID NO 12
<211> LENGTH: 368
<212> TYPE: PRT
<213> ORGANISM: Mycobacterium tuberculosis

<400> SEQUENCE: 12

Met Leu Trp His Ala Met Pro Pro Glu Leu Asn Thr Ala Arg Leu Met
1               5                   10                  15
Ala Gly Ala Gly Pro Ala Pro Met Leu Ala Ala Ala Gly Trp Gln
                20                  25                  30
Thr Leu Ser Ala Ala Leu Asp Ala Gln Ala Val Glu Leu Thr Ala Arg
            35                  40                  45
Leu Asn Ser Leu Gly Glu Ala Trp Thr Gly Gly Ser Asp Lys Ala
        50                  55                  60
Leu Ala Ala Thr Pro Met Val Val Trp Leu Gln Thr Ala Ser Thr
65                  70                  75                  80
Gln Ala Lys Thr Arg Ala Met Gln Ala Thr Gln Ala Ala Tyr
                85                  90                  95
Thr Gln Ala Met Ala Thr Thr Pro Ser Leu Pro Glu Ile Ala Ala Asn
                100                 105                 110
His Ile Thr Gln Ala Val Leu Thr Ala Thr Asn Phe Phe Gly Ile Asn
            115                 120                 125
Thr Ile Pro Ile Ala Leu Thr Glu Met Asp Tyr Phe Ile Arg Met Trp
        130                 135                 140
Asn Gln Ala Ala Leu Ala Met Glu Val Tyr Gln Ala Glu Thr Ala Val
145                 150                 155                 160
```

```
Asn Thr Leu Phe Glu Lys Leu Glu Pro Met Ala Ser Ile Leu Asp Pro
                165                 170                 175

Gly Ala Ser Gln Ser Thr Thr Asn Pro Ile Phe Gly Met Pro Ser Pro
            180                 185                 190

Gly Ser Ser Thr Pro Val Gly Gln Leu Pro Pro Ala Ala Thr Gln Thr
        195                 200                 205

Leu Gly Gln Leu Gly Glu Met Ser Gly Pro Met Gln Gln Leu Thr Gln
    210                 215                 220

Pro Leu Gln Gln Val Thr Ser Leu Phe Ser Gln Val Gly Gly Thr Gly
225                 230                 235                 240

Gly Gly Asn Pro Ala Asp Glu Glu Ala Ala Gln Met Gly Leu Leu Gly
                245                 250                 255

Thr Ser Pro Leu Ser Asn His Pro Leu Ala Gly Gly Ser Gly Pro Ser
            260                 265                 270

Ala Gly Ala Gly Leu Leu Arg Ala Glu Ser Leu Pro Gly Ala Gly Gly
        275                 280                 285

Ser Leu Thr Arg Thr Pro Leu Met Ser Gln Leu Ile Glu Lys Pro Val
    290                 295                 300

Ala Pro Ser Val Met Pro Ala Ala Ala Gly Ser Ser Ala Thr Gly
305                 310                 315                 320

Gly Ala Ala Pro Val Gly Ala Gly Ala Met Gly Gln Gly Ala Gln Ser
                325                 330                 335

Gly Gly Ser Thr Arg Pro Gly Leu Val Ala Pro Ala Pro Leu Ala Gln
            340                 345                 350

Glu Arg Glu Glu Asp Asp Glu Asp Asp Trp Asp Glu Glu Asp Asp Trp
        355                 360                 365

<210> SEQ ID NO 13
<211> LENGTH: 666
<212> TYPE: PRT
<213> ORGANISM: Mycobacterium tuberculosis

<400> SEQUENCE: 13

Met Ala Ala Asp Tyr Asp Lys Leu Phe Arg Pro His Glu Gly Met Glu
1               5                   10                  15

Ala Pro Asp Asp Met Ala Ala Gln Pro Phe Phe Asp Pro Ser Ala Ser
            20                  25                  30

Phe Pro Pro Ala Pro Ala Ser Ala Asn Leu Pro Lys Pro Asn Gly Gln
        35                  40                  45

Thr Pro Pro Pro Thr Ser Asp Asp Leu Ser Glu Arg Phe Val Ser Ala
    50                  55                  60

Pro Pro Pro Pro Pro Pro Pro Pro Pro Pro Thr Pro Met
65                  70                  75                  80

Pro Ile Ala Ala Gly Glu Pro Pro Ser Pro Glu Pro Ala Ala Ser Lys
                85                  90                  95

Pro Pro Thr Pro Pro Met Pro Ile Ala Gly Pro Glu Ala Pro Pro
            100                 105                 110

Lys Pro Pro Thr Pro Pro Met Pro Ile Ala Gly Pro Glu Ala Pro
        115                 120                 125

Pro Lys Pro Pro Thr Pro Pro Met Pro Ile Ala Gly Pro Ala Pro Thr
    130                 135                 140

Pro Thr Glu Ser Gln Leu Ala Pro Pro Arg Pro Pro Thr Pro Gln Thr
145                 150                 155                 160

Pro Thr Gly Ala Pro Gln Gln Pro Glu Ser Pro Ala Pro His Val Pro
```

```
                    165                 170                 175
Ser His Gly Pro His Gln Pro Arg Arg Thr Ala Pro Ala Pro Pro Trp
                180                 185                 190

Ala Lys Met Pro Ile Gly Glu Pro Pro Ala Pro Ser Arg Pro Ser
            195                 200                 205

Ala Ser Pro Ala Glu Pro Thr Arg Pro Ala Pro Gln His Ser Arg
        210                 215                 220

Arg Ala Arg Arg Gly His Arg Tyr Arg Thr Asp Thr Glu Arg Asn Val
225                 230                 235                 240

Gly Lys Val Ala Thr Gly Pro Ser Ile Gln Ala Arg Leu Arg Ala Glu
                245                 250                 255

Glu Ala Ser Gly Ala Gln Leu Ala Pro Gly Thr Glu Pro Ser Pro Ala
            260                 265                 270

Pro Leu Gly Gln Pro Arg Ser Tyr Leu Ala Pro Pro Thr Arg Pro Ala
        275                 280                 285

Pro Thr Glu Pro Pro Pro Ser Pro Ser Pro Gln Arg Asn Ser Gly Arg
    290                 295                 300

Arg Ala Glu Arg Arg Val His Pro Asp Leu Ala Ala Gln His Ala Ala
305                 310                 315                 320

Ala Gln Pro Asp Ser Ile Thr Ala Thr Thr Gly Gly Arg Arg Arg
                325                 330                 335

Lys Arg Ala Ala Pro Asp Leu Asp Ala Thr Gln Lys Ser Leu Arg Pro
            340                 345                 350

Ala Ala Lys Gly Pro Lys Val Lys Lys Val Lys Pro Gln Lys Pro Lys
        355                 360                 365

Ala Thr Lys Pro Pro Lys Val Val Ser Gln Arg Gly Trp Arg His Trp
    370                 375                 380

Val His Ala Leu Thr Arg Ile Asn Leu Gly Leu Ser Pro Asp Glu Lys
385                 390                 395                 400

Tyr Glu Leu Asp Leu His Ala Arg Val Arg Arg Asn Pro Arg Gly Ser
                405                 410                 415

Tyr Gln Ile Ala Val Val Gly Leu Lys Gly Gly Ala Gly Lys Thr Thr
            420                 425                 430

Leu Thr Ala Ala Leu Gly Ser Thr Leu Ala Gln Val Arg Ala Asp Arg
        435                 440                 445

Ile Leu Ala Leu Asp Ala Asp Pro Gly Ala Gly Asn Leu Ala Asp Arg
    450                 455                 460

Val Gly Arg Gln Ser Gly Ala Thr Ile Ala Asp Val Leu Ala Glu Lys
465                 470                 475                 480

Glu Leu Ser His Tyr Asn Asp Ile Arg Ala His Thr Ser Val Asn Ala
                485                 490                 495

Val Asn Leu Glu Val Leu Pro Ala Pro Glu Tyr Ser Ser Ala Gln Arg
            500                 505                 510

Ala Leu Ser Asp Ala Asp Trp His Phe Ile Ala Asp Pro Ala Ser Arg
        515                 520                 525

Phe Tyr Asn Leu Val Leu Ala Asp Cys Gly Ala Gly Phe Phe Asp Pro
    530                 535                 540

Leu Thr Arg Gly Val Leu Ser Thr Val Ser Gly Val Val Val Ala
545                 550                 555                 560

Ser Val Ser Ile Asp Gly Ala Gln Gln Ala Ser Val Ala Leu Asp Trp
                565                 570                 575

Leu Arg Asn Asn Gly Tyr Gln Asp Leu Ala Ser Arg Ala Cys Val Val
            580                 585                 590
```

```
Ile Asn His Ile Met Pro Gly Glu Pro Asn Val Ala Val Lys Asp Leu
            595                 600                 605
Val Arg His Phe Glu Gln Gln Val Gln Pro Gly Arg Val Val Val Met
        610                 615                 620
Pro Trp Asp Arg His Ile Ala Ala Gly Thr Glu Ile Ser Leu Asp Leu
625                 630                 635                 640
Leu Asp Pro Ile Tyr Lys Arg Lys Val Leu Glu Leu Ala Ala Ala Leu
                645                 650                 655
Ser Asp Asp Phe Glu Arg Ala Gly Arg Arg
            660                 665

<210> SEQ ID NO 14
<211> LENGTH: 511
<212> TYPE: PRT
<213> ORGANISM: Mycobacterium tuberculosis

<400> SEQUENCE: 14

Leu Ser Ala Pro Ala Val Ala Ala Gly Pro Thr Ala Ala Gly Ala Thr
1               5                   10                  15
Ala Ala Arg Pro Ala Thr Thr Arg Val Thr Ile Leu Thr Gly Arg Arg
            20                  25                  30
Met Thr Asp Leu Val Leu Pro Ala Ala Val Pro Met Glu Thr Tyr Ile
        35                  40                  45
Asp Asp Thr Val Ala Val Leu Ser Glu Val Leu Glu Asp Thr Pro Ala
    50                  55                  60
Asp Val Leu Gly Gly Phe Asp Phe Thr Ala Gln Gly Val Trp Ala Phe
65                  70                  75                  80
Ala Arg Pro Gly Ser Pro Pro Leu Lys Leu Asp Gln Ser Leu Asp Asp
                85                  90                  95
Ala Gly Val Val Asp Gly Ser Leu Leu Thr Leu Val Ser Val Ser Arg
            100                 105                 110
Thr Glu Arg Tyr Arg Pro Leu Val Glu Asp Val Ile Asp Ala Ile Ala
        115                 120                 125
Val Leu Asp Glu Ser Pro Glu Phe Asp Arg Thr Ala Leu Asn Arg Phe
    130                 135                 140
Val Gly Ala Ala Ile Pro Leu Leu Thr Ala Pro Val Ile Gly Met Ala
145                 150                 155                 160
Met Arg Ala Trp Trp Glu Thr Gly Arg Ser Leu Trp Trp Pro Leu Ala
                165                 170                 175
Ile Gly Ile Leu Gly Ile Ala Val Leu Val Gly Ser Phe Val Ala Asn
            180                 185                 190
Arg Phe Tyr Gln Ser Gly His Leu Ala Glu Cys Leu Leu Val Thr Thr
        195                 200                 205
Tyr Leu Leu Ile Ala Thr Ala Ala Leu Ala Val Pro Leu Pro Arg
    210                 215                 220
Gly Val Asn Ser Leu Gly Ala Pro Gln Val Ala Gly Ala Ala Thr Ala
225                 230                 235                 240
Val Leu Phe Leu Thr Leu Met Thr Arg Gly Gly Pro Arg Lys Arg His
                245                 250                 255
Glu Leu Ala Ser Phe Ala Val Ile Thr Ala Ile Ala Val Ile Ala Ala
            260                 265                 270
Ala Ala Ala Phe Gly Tyr Gly Tyr Gln Asp Trp Val Pro Ala Gly Gly
        275                 280                 285
Ile Ala Phe Gly Leu Phe Ile Val Thr Asn Ala Ala Lys Leu Thr Val
```

```
                290                 295                 300
Ala Val Ala Arg Ile Ala Leu Pro Pro Ile Pro Val Pro Gly Glu Thr
305                 310                 315                 320

Val Asp Asn Glu Glu Leu Leu Asp Pro Val Ala Thr Pro Glu Ala Thr
                325                 330                 335

Ser Glu Glu Thr Pro Thr Trp Gln Ala Ile Ile Ala Ser Val Pro Ala
                340                 345                 350

Ser Ala Val Arg Leu Thr Glu Arg Ser Lys Leu Ala Lys Gln Leu Leu
                355                 360                 365

Ile Gly Tyr Val Thr Ser Gly Thr Leu Ile Leu Ala Ala Gly Ala Ile
                370                 375                 380

Ala Val Val Val Arg Gly His Phe Phe Val His Ser Leu Val Val Ala
385                 390                 395                 400

Gly Leu Ile Thr Thr Val Cys Gly Phe Arg Ser Arg Leu Tyr Ala Glu
                405                 410                 415

Arg Trp Cys Ala Trp Ala Leu Leu Ala Ala Thr Val Ala Ile Pro Thr
                420                 425                 430

Gly Leu Thr Ala Lys Leu Ile Ile Trp Tyr Pro His Tyr Ala Trp Leu
                435                 440                 445

Leu Leu Ser Val Tyr Leu Thr Val Ala Leu Val Ala Leu Val Val Val
                450                 455                 460

Gly Ser Met Ala His Val Arg Arg Val Ser Pro Val Val Lys Arg Thr
465                 470                 475                 480

Leu Glu Leu Ile Asp Gly Ala Met Ile Ala Ala Ile Ile Pro Met Leu
                485                 490                 495

Leu Trp Ile Thr Gly Val Tyr Asp Thr Val Arg Asn Ile Arg Phe
                500                 505                 510

<210> SEQ ID NO 15
<211> LENGTH: 280
<212> TYPE: PRT
<213> ORGANISM: Mycobacterium tuberculosis

<400> SEQUENCE: 15

Met Ala Glu Pro Leu Ala Val Asp Pro Thr Gly Leu Ser Ala Ala
1               5                   10                  15

Ala Lys Leu Ala Gly Leu Val Phe Pro Gln Pro Ala Pro Ile Ala
                20                  25                  30

Val Ser Gly Thr Asp Ser Val Ala Ala Ile Asn Glu Thr Met Pro
                35                  40                  45

Ser Ile Glu Ser Leu Val Ser Asp Gly Leu Pro Gly Val Lys Ala Ala
50                  55                  60

Leu Thr Arg Thr Ala Ser Asn Met Asn Ala Ala Ala Asp Val Tyr Ala
65                  70                  75                  80

Lys Thr Asp Gln Ser Leu Gly Thr Ser Leu Ser Gln Tyr Ala Phe Gly
                85                  90                  95

Ser Ser Gly Glu Gly Leu Ala Gly Val Ala Ser Val Gly Gly Gln Pro
                100                 105                 110

Ser Gln Ala Thr Gln Leu Leu Ser Thr Pro Val Ser Gln Val Thr Thr
                115                 120                 125

Gln Leu Gly Glu Thr Ala Ala Glu Leu Ala Pro Arg Val Val Ala Thr
                130                 135                 140

Val Pro Gln Leu Val Gln Leu Ala Pro His Ala Val Gln Met Ser Gln
145                 150                 155                 160
```

```
Asn Ala Ser Pro Ile Ala Gln Thr Ile Ser Gln Thr Ala Gln Gln Ala
            165                 170                 175

Ala Gln Ser Ala Gln Gly Gly Ser Gly Pro Met Pro Ala Gln Leu Ala
        180                 185                 190

Ser Ala Glu Lys Pro Ala Thr Glu Gln Ala Glu Pro Val His Glu Val
        195                 200                 205

Thr Asn Asp Asp Gln Gly Asp Gln Gly Asp Val Gln Pro Ala Glu Val
    210                 215                 220

Val Ala Ala Ala Arg Asp Glu Gly Ala Gly Ser Pro Gly Gln Gln
225                 230                 235                 240

Pro Gly Gly Gly Val Pro Ala Gln Ala Met Asp Thr Gly Ala Gly Ala
                245                 250                 255

Arg Pro Ala Ala Ser Pro Leu Ala Ala Pro Val Asp Pro Ser Thr Pro
            260                 265                 270

Ala Pro Ser Thr Thr Thr Thr Leu
            275                 280

<210> SEQ ID NO 16
<211> LENGTH: 729
<212> TYPE: PRT
<213> ORGANISM: Mycobacterium tuberculosis

<400> SEQUENCE: 16

Met Ser Ile Thr Arg Pro Thr Gly Ser Tyr Ala Arg Gln Met Leu Asp
1               5                   10                  15

Pro Gly Gly Trp Val Glu Ala Asp Glu Asp Thr Phe Tyr Asp Arg Ala
            20                  25                  30

Gln Glu Tyr Ser Gln Val Leu Gln Arg Val Thr Asp Val Leu Asp Thr
        35                  40                  45

Cys Arg Gln Gln Lys Gly His Val Phe Glu Gly Gly Leu Trp Ser Gly
    50                  55                  60

Gly Ala Ala Asn Ala Ala Asn Gly Ala Leu Gly Ala Asn Ile Asn Gln
65              70                  75                  80

Leu Met Thr Leu Gln Asp Tyr Leu Ala Thr Val Ile Thr Trp His Arg
                85                  90                  95

His Ile Ala Gly Leu Ile Glu Gln Ala Lys Ser Asp Ile Gly Asn Asn
            100                 105                 110

Val Asp Gly Ala Gln Arg Glu Ile Asp Ile Leu Glu Asn Asp Pro Ser
        115                 120                 125

Leu Asp Ala Asp Glu Arg His Thr Ala Ile Asn Ser Leu Val Thr Ala
    130                 135                 140

Thr His Gly Ala Asn Val Ser Leu Val Ala Glu Thr Ala Glu Arg Val
145                 150                 155                 160

Leu Glu Ser Lys Asn Trp Lys Pro Pro Lys Asn Ala Leu Glu Asp Leu
                165                 170                 175

Leu Gln Gln Lys Ser Pro Pro Pro Asp Val Pro Thr Leu Val Val
            180                 185                 190

Pro Ser Pro Gly Thr Pro Gly Thr Pro Gly Thr Pro Ile Thr Pro Gly
        195                 200                 205

Thr Pro Ile Thr Pro Gly Thr Pro Ile Thr Pro Ile Pro Gly Ala Pro
    210                 215                 220

Val Thr Pro Ile Thr Pro Thr Pro Gly Thr Pro Val Thr Pro Val Thr
225                 230                 235                 240

Pro Gly Lys Pro Val Thr Pro Val Thr Pro Val Lys Pro Gly Thr Pro
                245                 250                 255
```

```
Gly Glu Pro Thr Pro Ile Thr Pro Val Thr Pro Val Ala Pro Ala
            260             265             270

Thr Pro Ala Thr Pro Ala Thr Pro Val Thr Pro Ala Pro Ala Pro His
            275             280             285

Pro Gln Pro Ala Pro Ala Pro Ser Pro Gly Pro Gln Pro Val
    290             295             300

Thr Pro Ala Thr Pro Gly Pro Ser Gly Pro Ala Thr Pro Gly Thr Pro
305             310             315             320

Gly Gly Glu Pro Ala Pro His Val Lys Pro Ala Ala Leu Ala Glu Gln
                325             330             335

Pro Gly Val Pro Gly Gln His Ala Gly Gly Thr Gln Ser Gly Pro
        340             345             350

Ala His Ala Asp Glu Ser Ala Ala Ser Val Thr Pro Ala Ala Ser
        355             360             365

Gly Val Pro Gly Ala Arg Ala Ala Ala Ala Pro Ser Gly Thr Ala
    370             375             380

Val Gly Ala Gly Ala Arg Ser Ser Val Gly Thr Ala Ala Ser Gly
385             390             395             400

Ala Gly Ser His Ala Ala Thr Gly Arg Ala Pro Val Ala Thr Ser Asp
                405             410             415

Lys Ala Ala Ala Pro Ser Thr Arg Ala Ala Ser Ala Arg Thr Ala Pro
            420             425             430

Pro Ala Arg Pro Pro Ser Thr Asp His Ile Asp Lys Pro Asp Arg Ser
            435             440             445

Glu Ser Ala Asp Asp Gly Thr Pro Val Ser Met Ile Pro Val Ser Ala
    450             455             460

Ala Arg Ala Ala Arg Asp Ala Ala Thr Ala Ala Ala Ser Ala Arg Gln
465             470             475             480

Arg Gly Arg Gly Asp Ala Leu Arg Leu Ala Arg Arg Ile Ala Ala Ala
            485             490             495

Leu Asn Ala Ser Asp Asn Asn Ala Gly Asp Tyr Gly Phe Phe Trp Ile
            500             505             510

Thr Ala Val Thr Thr Asp Gly Ser Ile Val Val Ala Asn Ser Tyr Gly
            515             520             525

Leu Ala Tyr Ile Pro Asp Gly Met Glu Leu Pro Asn Lys Val Tyr Leu
            530             535             540

Ala Ser Ala Asp His Ala Ile Pro Val Asp Glu Ile Ala Arg Cys Ala
545             550             555             560

Thr Tyr Pro Val Leu Ala Val Gln Ala Trp Ala Ala Phe His Asp Met
            565             570             575

Thr Leu Arg Ala Val Ile Gly Thr Ala Glu Gln Leu Ala Ser Ser Asp
            580             585             590

Pro Gly Val Ala Lys Ile Val Leu Glu Pro Asp Asp Ile Pro Glu Ser
            595             600             605

Gly Lys Met Thr Gly Arg Ser Arg Leu Glu Val Val Asp Pro Ser Ala
            610             615             620

Ala Ala Gln Leu Ala Asp Thr Thr Asp Gln Arg Leu Leu Asp Leu Leu
625             630             635             640

Pro Pro Ala Pro Val Asp Val Asn Pro Pro Gly Asp Glu Arg His Met
            645             650             655

Leu Trp Phe Glu Leu Met Lys Pro Met Thr Ser Thr Ala Thr Gly Arg
            660             665             670
```

```
Glu Ala Ala His Leu Arg Ala Phe Arg Ala Tyr Ala Ala His Ser Gln
            675                 680                 685

Glu Ile Ala Leu His Gln Ala His Thr Ala Thr Asp Ala Ala Val Gln
        690                 695                 700

Arg Val Ala Val Ala Asp Trp Leu Tyr Trp Gln Tyr Val Thr Gly Leu
705                 710                 715                 720

Leu Asp Arg Ala Leu Ala Ala Cys
                725

<210> SEQ ID NO 17
<211> LENGTH: 115
<212> TYPE: PRT
<213> ORGANISM: Mycobacterium tuberculosis

<400> SEQUENCE: 17

Val Ser Met Asp Glu Leu Asp Pro His Val Ala Arg Ala Leu Thr Leu
1               5                   10                  15

Ala Ala Arg Phe Gln Ser Ala Leu Asp Gly Thr Leu Asn Gln Met Asn
            20                  25                  30

Asn Gly Ser Phe Arg Ala Thr Asp Glu Ala Glu Thr Val Glu Val Thr
        35                  40                  45

Ile Asn Gly His Gln Trp Leu Thr Gly Leu Arg Ile Glu Asp Gly Leu
    50                  55                  60

Leu Lys Lys Leu Gly Ala Glu Val Ala Gln Arg Val Asn Glu Ala
65                  70                  75                  80

Leu His Asn Ala Gln Ala Ala Ser Ala Tyr Asn Asp Ala Ala Gly
                85                  90                  95

Glu Gln Leu Thr Ala Ala Leu Ser Ala Met Ser Arg Ala Met Asn Glu
            100                 105                 110

Gly Met Ala
        115

<210> SEQ ID NO 18
<211> LENGTH: 460
<212> TYPE: PRT
<213> ORGANISM: Mycobacterium tuberculosis

<400> SEQUENCE: 18

Met Thr Gln Ser Gln Thr Val Thr Val Asp Gln Gln Glu Ile Leu Asn
1               5                   10                  15

Arg Ala Asn Glu Val Glu Ala Pro Met Ala Asp Pro Thr Asp Val
            20                  25                  30

Pro Ile Thr Pro Cys Glu Leu Thr Ala Ala Lys Asn Ala Ala Gln Gln
        35                  40                  45

Leu Val Leu Ser Ala Asp Asn Met Arg Glu Tyr Leu Ala Ala Gly Ala
    50                  55                  60

Lys Glu Arg Gln Arg Leu Ala Thr Ser Leu Arg Asn Ala Ala Lys Ala
65                  70                  75                  80

Tyr Gly Glu Val Asp Glu Ala Ala Thr Ala Leu Asp Asn Asp Gly
                85                  90                  95

Glu Gly Thr Val Gln Ala Glu Ser Ala Gly Ala Val Gly Gly Asp Ser
            100                 105                 110

Ser Ala Glu Leu Thr Asp Thr Pro Arg Val Ala Thr Ala Gly Glu Pro
        115                 120                 125

Asn Phe Met Asp Leu Lys Glu Ala Ala Arg Lys Leu Glu Thr Gly Asp
    130                 135                 140
```

```
Gln Gly Ala Ser Leu Ala His Phe Ala Asp Gly Trp Asn Thr Phe Asn
145                 150                 155                 160

Leu Thr Leu Gln Gly Asp Val Lys Arg Phe Arg Gly Phe Asp Asn Trp
            165                 170                 175

Glu Gly Asp Ala Ala Thr Ala Cys Glu Ala Ser Leu Asp Gln Gln Arg
        180                 185                 190

Gln Trp Ile Leu His Met Ala Lys Leu Ser Ala Ala Met Ala Lys Gln
    195                 200                 205

Ala Gln Tyr Val Ala Gln Leu His Val Trp Ala Arg Arg Glu His Pro
210                 215                 220

Thr Tyr Glu Asp Ile Val Gly Leu Glu Arg Leu Tyr Ala Glu Asn Pro
225                 230                 235                 240

Ser Ala Arg Asp Gln Ile Leu Pro Val Tyr Ala Glu Tyr Gln Gln Arg
            245                 250                 255

Ser Glu Lys Val Leu Thr Glu Tyr Asn Asn Lys Ala Ala Leu Glu Pro
        260                 265                 270

Val Asn Pro Pro Lys Pro Pro Ala Ile Lys Ile Asp Pro Pro Pro
    275                 280                 285

Pro Pro Gln Glu Gln Gly Leu Ile Pro Gly Phe Leu Met Pro Pro Ser
290                 295                 300

Asp Gly Ser Gly Val Thr Pro Gly Thr Gly Met Pro Ala Ala Pro Met
305                 310                 315                 320

Val Pro Pro Thr Gly Ser Pro Gly Gly Gly Leu Pro Ala Asp Thr Ala
            325                 330                 335

Ala Gln Leu Thr Ser Ala Gly Arg Glu Ala Ala Leu Ser Gly Asp
        340                 345                 350

Val Ala Val Lys Ala Ala Ser Leu Gly Gly Gly Gly Gly Gly Val
            355                 360                 365

Pro Ser Ala Pro Leu Gly Ser Ala Ile Gly Gly Ala Glu Ser Val Arg
370                 375                 380

Pro Ala Gly Ala Gly Asp Ile Ala Gly Leu Gly Gln Gly Arg Ala Gly
385                 390                 395                 400

Gly Gly Ala Ala Leu Gly Gly Gly Met Gly Met Pro Met Gly Ala
            405                 410                 415

Ala His Gln Gly Gln Gly Ala Lys Ser Lys Gly Ser Gln Gln Glu
        420                 425                 430

Asp Glu Ala Leu Tyr Thr Glu Asp Arg Ala Trp Thr Glu Ala Val Ile
            435                 440                 445

Gly Asn Arg Arg Arg Gln Asp Ser Lys Glu Ser Lys
450                 455                 460

<210> SEQ ID NO 19
<211> LENGTH: 15
<212> TYPE: PRT
<213> ORGANISM: Mycobacterium tuberculosis

<400> SEQUENCE: 19

Met Thr Glu Gln Gln Trp Asn Phe Ala Gly Ile Glu Ala Ala Ala
1               5                   10                  15

<210> SEQ ID NO 20
<211> LENGTH: 15
<212> TYPE: PRT
<213> ORGANISM: Mycobacterium tuberculosis

<400> SEQUENCE: 20
```

```
Asn Phe Ala Gly Ile Glu Ala Ala Ala Ser Ala Ile Gln Gly Asn
1               5                  10                  15
```

<210> SEQ ID NO 21
<211> LENGTH: 15
<212> TYPE: PRT
<213> ORGANISM: Mycobacterium tuberculosis

<400> SEQUENCE: 21

```
Ala Ser Ala Ile Gln Gly Asn Val Thr Ser Ile His Ser Leu Leu
1               5                  10                  15
```

<210> SEQ ID NO 22
<211> LENGTH: 15
<212> TYPE: PRT
<213> ORGANISM: Mycobacterium tuberculosis

<400> SEQUENCE: 22

```
Asn Val Thr Ser Ile His Ser Leu Leu Asp Glu Gly Lys Gln Ser
1               5                  10                  15
```

<210> SEQ ID NO 23
<211> LENGTH: 15
<212> TYPE: PRT
<213> ORGANISM: Mycobacterium tuberculosis

<400> SEQUENCE: 23

```
Ser Leu Leu Asp Glu Gly Lys Gln Ser Leu Thr Lys Leu Ala Ala
1               5                  10                  15
```

<210> SEQ ID NO 24
<211> LENGTH: 15
<212> TYPE: PRT
<213> ORGANISM: Mycobacterium tuberculosis

<400> SEQUENCE: 24

```
Lys Gln Ser Leu Thr Lys Leu Ala Ala Ala Trp Gly Gly Ser Gly
1               5                  10                  15
```

<210> SEQ ID NO 25
<211> LENGTH: 15
<212> TYPE: PRT
<213> ORGANISM: Mycobacterium tuberculosis

<400> SEQUENCE: 25

```
Ala Ala Trp Gly Gly Ser Gly Ser Glu Ala Tyr Gln Gly Val Gln
1               5                  10                  15
```

<210> SEQ ID NO 26
<211> LENGTH: 15
<212> TYPE: PRT
<213> ORGANISM: Mycobacterium tuberculosis

<400> SEQUENCE: 26

```
Gly Ser Glu Ala Tyr Gln Gly Val Gln Gln Lys Trp Asp Ala Thr
1               5                  10                  15
```

<210> SEQ ID NO 27
<211> LENGTH: 15
<212> TYPE: PRT
<213> ORGANISM: Mycobacterium tuberculosis

<400> SEQUENCE: 27

```
Gln Gln Lys Trp Asp Ala Thr Ala Thr Glu Leu Asn Asn Ala Leu
1               5                  10                  15
```

<210> SEQ ID NO 28
<211> LENGTH: 15
<212> TYPE: PRT
<213> ORGANISM: Mycobacterium tuberculosis

<400> SEQUENCE: 28

Thr Ala Thr Glu Leu Asn Asn Ala Leu Gln Asn Leu Ala Arg Thr
1               5                   10                  15

<210> SEQ ID NO 29
<211> LENGTH: 15
<212> TYPE: PRT
<213> ORGANISM: Mycobacterium tuberculosis

<400> SEQUENCE: 29

Ala Leu Gln Asn Leu Ala Arg Thr Ile Ser Glu Ala Gly Gln Ala
1               5                   10                  15

<210> SEQ ID NO 30
<211> LENGTH: 15
<212> TYPE: PRT
<213> ORGANISM: Mycobacterium tuberculosis

<400> SEQUENCE: 30

Thr Ile Ser Glu Ala Gly Gln Ala Met Ala Ser Thr Glu Gly Asn
1               5                   10                  15

<210> SEQ ID NO 31
<211> LENGTH: 15
<212> TYPE: PRT
<213> ORGANISM: Mycobacterium tuberculosis

<400> SEQUENCE: 31

Gln Ala Met Ala Ser Thr Glu Gly Asn Val Thr Gly Met Phe Ala
1               5                   10                  15

<210> SEQ ID NO 32
<211> LENGTH: 462
<212> TYPE: PRT
<213> ORGANISM: Mycobacterium tuberculosis

<400> SEQUENCE: 32

Met Arg Asn Pro Leu Gly Leu Arg Phe Ser Thr Gly His Ala Leu Leu
1               5                   10                  15

Ala Ser Ala Leu Ala Pro Pro Cys Ile Ile Ala Phe Leu Glu Thr Arg
            20                  25                  30

Tyr Trp Trp Ala Gly Ile Ala Leu Ala Ser Leu Gly Val Ile Val Ala
        35                  40                  45

Thr Val Thr Phe Tyr Gly Arg Arg Ile Thr Gly Trp Val Ala Ala Val
    50                  55                  60

Tyr Ala Trp Leu Arg Arg Arg Arg Pro Asp Ser Ser Ser Glu
65                  70                  75                  80

Pro Val Val Gly Ala Thr Val Lys Pro Gly Asp His Val Ala Val Arg
                85                  90                  95

Trp Gln Gly Glu Phe Leu Val Ala Val Ile Glu Leu Ile Pro Arg Pro
            100                 105                 110

Phe Thr Pro Thr Val Ile Val Asp Gly Gln Ala His Thr Asp Asp Met
        115                 120                 125

Leu Asp Thr Gly Leu Val Glu Glu Leu Leu Ser Val His Cys Pro Asp
    130                 135                 140

-continued

```
Leu Glu Ala Asp Ile Val Ser Ala Gly Tyr Arg Val Gly Asn Thr Ala
145                 150                 155                 160

Ala Pro Asp Val Val Ser Leu Tyr Gln Gln Val Ile Gly Thr Asp Pro
                165                 170                 175

Ala Pro Ala Asn Arg Arg Thr Trp Ile Val Leu Arg Ala Asp Pro Glu
            180                 185                 190

Arg Thr Arg Lys Ser Ala Gln Arg Asp Glu Gly Val Ala Gly Leu
        195                 200                 205

Ala Arg Tyr Leu Val Ala Ser Ala Thr Arg Ile Ala Asp Arg Leu Ala
210                 215                 220

Ser His Gly Val Asp Ala Val Cys Gly Arg Ser Phe Asp Tyr Asp
225                 230                 235                 240

His Ala Thr Asp Ile Gly Phe Val Arg Glu Lys Trp Ser Met Ile Lys
                245                 250                 255

Gly Arg Asp Ala Tyr Thr Ala Ala Tyr Ala Ala Pro Gly Gly Pro Asp
            260                 265                 270

Val Trp Trp Ser Ala Arg Ala Asp His Thr Ile Thr Arg Val Arg Val
        275                 280                 285

Ala Pro Gly Met Ala Pro Gln Ser Thr Val Leu Leu Thr Thr Ala Asp
290                 295                 300

Lys Pro Lys Thr Pro Arg Gly Phe Ala Arg Leu Phe Gly Gly Gln Arg
305                 310                 315                 320

Pro Ala Leu Gln Gly Gln His Leu Val Ala Asn Arg His Cys Gln Leu
            325                 330                 335

Pro Ile Gly Ser Ala Gly Val Leu Val Gly Glu Thr Val Asn Arg Cys
        340                 345                 350

Pro Val Tyr Met Pro Phe Asp Asp Val Asp Ile Ala Leu Asn Leu Gly
    355                 360                 365

Asp Ala Gln Thr Phe Thr Gln Phe Val Arg Ala Ala Ala Gly
370                 375                 380

Ala Met Val Thr Val Gly Pro Gln Phe Glu Glu Phe Ala Arg Leu Ile
385                 390                 395                 400

Gly Ala His Ile Gly Gln Glu Val Lys Val Ala Trp Pro Asn Ala Thr
            405                 410                 415

Thr Tyr Leu Gly Pro His Pro Gly Ile Asp Arg Val Ile Leu Arg His
        420                 425                 430

Asn Val Ile Gly Thr Pro Arg His Arg Gln Leu Pro Ile Arg Arg Val
    435                 440                 445

Ser Pro Pro Glu Glu Ser Arg Tyr Gln Met Ala Leu Pro Lys
450                 455                 460

<210> SEQ ID NO 33
<211> LENGTH: 446
<212> TYPE: PRT
<213> ORGANISM: Mycobacterium tuberculosis

<400> SEQUENCE: 33

Val His Arg Ile Phe Leu Ile Thr Val Ala Leu Ala Leu Leu Thr Ala
1               5                   10                  15

Ser Pro Ala Ser Ala Ile Thr Pro Pro Ile Asp Pro Gly Ala Leu
                20                  25                  30

Pro Pro Asp Val Thr Gly Pro Asp Gln Pro Thr Glu Gln Arg Val Leu
            35                  40                  45

Cys Ala Ser Pro Thr Thr Leu Pro Gly Ser Gly Phe His Asp Pro Pro
```

```
                50                  55                  60
Trp Ser Asn Thr Tyr Leu Gly Val Ala Asp Ala His Lys Phe Ala Thr
 65                  70                  75                  80

Gly Ala Gly Val Thr Val Ala Val Ile Asp Thr Gly Val Asp Ala Ser
                 85                  90                  95

Pro Arg Val Pro Ala Glu Pro Gly Asp Phe Val Asp Gln Ala Gly
            100                 105                 110

Asn Gly Leu Ser Asp Cys Asp Ala His Gly Thr Leu Thr Ala Ser Ile
            115                 120                 125

Ile Ala Gly Arg Pro Ala Pro Thr Asp Gly Phe Val Gly Val Ala Pro
130                 135                 140

Asp Ala Arg Leu Leu Ser Leu Arg Gln Thr Ser Glu Ala Phe Glu Pro
145                 150                 155                 160

Val Gly Ser Gln Ala Asn Pro Asn Asp Pro Asn Ala Thr Pro Ala Ala
                165                 170                 175

Gly Ser Ile Arg Ser Leu Ala Arg Ala Val His Ala Ala Asn Leu
            180                 185                 190

Gly Val Gly Val Ile Asn Ile Ser Glu Ala Ala Cys Tyr Lys Val Ser
            195                 200                 205

Arg Pro Ile Asp Glu Thr Ser Leu Gly Ala Ser Ile Asp Tyr Ala Val
210                 215                 220

Asn Val Lys Gly Val Val Val Val Ala Ala Gly Asn Thr Gly Gly
225                 230                 235                 240

Asp Cys Val Gln Asn Pro Ala Pro Asp Pro Ser Thr Pro Gly Asp Pro
            245                 250                 255

Arg Gly Trp Asn Asn Val Gln Thr Val Val Thr Pro Ala Trp Tyr Ala
            260                 265                 270

Pro Leu Val Leu Ser Val Gly Gly Ile Gly Gln Thr Gly Met Pro Ser
            275                 280                 285

Ser Phe Ser Met His Gly Pro Trp Val Asp Val Ala Ala Pro Ala Glu
            290                 295                 300

Asn Ile Val Ala Leu Gly Asp Thr Gly Glu Pro Val Asn Ala Leu Gln
305                 310                 315                 320

Gly Arg Glu Gly Pro Val Pro Ile Ala Gly Thr Ser Phe Ala Ala Ala
                325                 330                 335

Tyr Val Ser Gly Leu Ala Ala Leu Leu Arg Gln Arg Phe Pro Asp Leu
            340                 345                 350

Thr Pro Ala Gln Ile Ile His Arg Ile Thr Ala Thr Ala Arg His Pro
            355                 360                 365

Gly Gly Gly Val Asp Asp Leu Val Gly Ala Gly Val Ile Asp Ala Val
370                 375                 380

Ala Ala Leu Thr Trp Asp Ile Pro Pro Gly Ala Ser Ala Pro Tyr
385                 390                 395                 400

Asn Val Arg Arg Leu Pro Pro Val Val Glu Pro Gly Pro Asp Arg
            405                 410                 415

Arg Pro Ile Thr Ala Val Ala Leu Val Ala Val Gly Leu Thr Leu Ala
            420                 425                 430

Leu Gly Leu Gly Ala Leu Ala Arg Arg Ala Leu Ser Arg Arg
            435                 440                 445

<210> SEQ ID NO 34
<211> LENGTH: 103
<212> TYPE: PRT
<213> ORGANISM: Mycobacterium tuberculosis
```

-continued

```
<400> SEQUENCE: 34

Met Thr Gly Phe Leu Gly Val Val Pro Ser Phe Leu Lys Val Leu Ala
1               5                   10                  15

Gly Met His Asn Glu Ile Val Gly Asp Ile Lys Arg Ala Thr Asp Thr
                20                  25                  30

Val Ala Gly Ile Ser Gly Arg Val Gln Leu Thr His Gly Ser Phe Thr
            35                  40                  45

Ser Lys Phe Asn Asp Thr Leu Gln Glu Phe Glu Thr Thr Arg Ser Ser
        50                  55                  60

Thr Gly Thr Gly Leu Gln Gly Val Thr Ser Gly Leu Ala Asn Asn Leu
65                  70                  75                  80

Leu Ala Ala Ala Gly Ala Tyr Leu Lys Ala Asp Asp Gly Leu Ala Gly
                85                  90                  95

Val Ile Asp Lys Ile Phe Gly
                100
```

TUBERCULOSIS TB VACCINE TO PREVENT REACTIVATION

CROSS REFERENCE TO RELATED APPLICATIONS

This application claims the benefit and priority to and is a U.S. National Phase Application of PCT International Application Number PCT/DK2010/000054, filed on Apr. 23, 2010, designating the United States of America and published in the English language, which is an International Application of and claims the benefit of priority to Danish Patent Application No. PA 2009 00539, filed on Apr. 24, 2009. The disclosures of the above-referenced applications are hereby expressly incorporated by reference in their entireties.

FIELD OF INVENTION

The present invention discloses a vaccine that can be administered to latently infected individuals to prevent reactivation of latent tuberculosis infection caused by species of the tuberculosis complex microorganisms (*Mycobacterium tuberculosis, M. bovis, M. africanum*), by targeting constitutively expressed antigens such as ESAT6, CFP10 and other antigens from the ESX-1 secretion system.

GENERAL BACKGROUND

Human tuberculosis caused by *Mycobacterium tuberculosis* (*M. tuberculosis*) is a severe global health problem, responsible for approx. 3 million deaths annually, according to the WHO. The worldwide incidence of new tuberculosis (TB) cases had been falling during the 1960s and 1970s but during recent decades this trend has markedly changed in part due to the advent of AIDS and the appearance of multidrug resistant strains of *M. tuberculosis*.

Organisms of the tuberculosis complex can cause a variety of diseases, but the commonest route of invasion is by inhalation of bacteria. This initiates an infection in the lung, which can ultimately spread to other parts of the body. Normally, this infection is restricted in growth by the immune system, so that the majority of infected individuals show few signs apart from cough and fever, which eventually abates. Approximately 30% of individuals are unable to contain the infection and they will develop primary disease, which in many cases will eventually prove fatal. However, it is believed that even those individuals who apparently control the infection remain infected, probably for the rest of their life. Certainly, individuals who have been healthy for years or even decades can suddenly develop tuberculosis, which has proven to be caused by the same organism they were infected with many years previously. *M. tuberculosis* and other organisms of the TB complex are unique in that the mycobacteria can evade the immune response and survive for long periods in a refractory non-replicating or slowly-replicating stage. This is referred to as latent TB and is at present a very significant global health problem which is estimated to affect approximately ⅓ of the world's population (Anon., 2001).

The only vaccine presently available for clinical use is BCG, a vaccine whose efficacy remains a matter of controversy. Although BCG consistently performs well in animal models of primary infection, it has clearly failed to control the TB epidemic. Consistent with that, BCG vaccination appears to provide protection against pediatric TB (which is due to primary infection), while offering little or no protection against adult disease (which is often reactivation of latent infection acquired in childhood). It has also been shown that vaccination of individuals who are currently sensitized to mycobacteria or latently infected is ineffective.

The course of a *M. tuberculosis* infection runs essentially through 3 phases, as illustrated in FIG. 1. During the acute phase, the bacteria proliferate in the organs, until the immune response increases to the point at which it can control the infection whereupon the bacterial load peaks and starts declining. After this, a latent phase is established where the bacterial load is kept stable at a low level. In this phase it has been the current thinking that *M. tuberculosis* goes from active multiplication to a state of dormancy, essentially becoming non-replicating and remaining inside the granuloma.

However, recently it has become clear that even in the stage of infection characterized by constant low bacterial numbers at least part of the bacterial population remain in a state of active metabolism (Talaat A M et al. 2007). These bacteria therefore survive, maintain an active metabolism and replicate in the face of a strong immune response. In the infected individual there is therefore a balance between non-replicating bacteria (that may be very difficult for the immune system to detect as they are located intracellularly) and slowly replicating bacteria that has an active but changed expression profile in an attempt to adapt to the hostile environment encountered in the immune host. Bacteria in this stage are typically not targeted by most of the preventive vaccines that are currently under development in the TB field as exemplified by the lack of activity when classical preventive vaccines are given to latently infected experimental animals (Turner 2000).

In some cases, the balance is tilted in favor of the pathogen and the infection goes into the reactivation phase, where the bacteria start replicating rapidly and bacterial numbers in the infected individual increases. Bacteria that replicates in latently infected individuals under very strong immune pressure is the target for the vaccination strategy in the present invention. Bacteria in this latent infective stage are typically not targeted by most of the preventive vaccines that are currently under development in the TB field as exemplified by the lack of activity when preventive vaccines are given to latently infected experimental animals (Turner et al 2000). This is not surprising as it is now known that a strong host immune response results in the down regulation of many antigens such as the major preventive vaccine antigen Ag85 and PstS (Rogerson, B J et al 2006). For Ag85B it has been shown that after infection there is an initial transient increase in Ag85B expression but already after two weeks infection the level of bacterial Ag85B expression had dropped from 0.3 transcripts per CFU of M.t.b. during the peak period to 0.02 transcripts per CFU and this low level is maintained at least up to 100 days post infection. Thus at any time point after week 2 of infection less than 2% of the bacteria actively express Ag85B (ibid.). The low expression of Ag85B is supported by a rapid drop in the number of T cells capable of making IFN-γ in response to Ag85B in the lung 3 weeks post infection or later.

In contrast some antigens are more stably (constitutively) expressed throughout the different stages of infection and one example of this is ESAT6. After the initial infection phase the ESAT-6 expression level stabilizes at 0.8 transcrips per CFU *M. tuberculosis*. This is a transcription level much higher than for Ag85B and this level is maintained stably up to at least 100 days post infection (Rogerson, B J et al 2006). Again transcription data is supported by immune data that shows strong T cell recognition of ESAT-6 at the later stages of infection at the site of infection (ibid.). This constitutive expression pattern is an important feature that illustrates that these molecules fulfills essential functions of crucial importance for the pathogen, functions that depends upon genes that needs to be constitutively expressed for the pathogen to survive in the immune host. These molecules are the basis for the current invention and are particularly important antigens for vaccines administered to latently infected individuals as they targets all stages of the bacterial lifestyle and therefore has the broadest possible basis for activity. This is different from current thinking that has been focused on identifying the antigens upregulated by mycobacteria during non-replicating persistence (Andersen, P. 2007, WO02048391, WO04006952, Lin M Y and Ottenhoff T H 2008; Leyten E M. et al. 2006). Although such antigens are upregulated during non-replicating persistence they may not always be available for immune recognition as the amounts available from non-replicating bacteria are below a reasonable threshold for detection or for the triggering of protective immune effector functions.

In contrast, several of the proteins from the ESX-1 secretion system have been shown to be highly immunogenic and expressed at high levels. ESX-1 is conserved in several pathogenic mycobacteria and involved in virulence of tubercle bacilli. The contribution of the individual ESX-1 proteins in secretion of ESAT-6, CFP10 and EspA has been well documented (Pym A S et al 2003; Guinn K I et al, 2004; Stanley, S A et al. 2003; Brodin, P. et al. 2006; MacGurn J A et al. 2005; Raghavan, S. et al. 2008) and the function of the effector molecules has been shown to be membrane lysis, escape from the phagosome and bacterial spreading (Gao L Y et al 2004; Smith J. et al. 2008).

The full nature of the immune response that controls latent infection and the factors that lead to reactivation are largely unknown. However, there is some evidence for a shift in the dominant cell types responsible. While CD4 T cells are essential and sufficient for control of infection during the acute phase, studies suggest that CD8 T cell responses are more important in the latent phase (van Pinxteren L A et al. 2000).

As one skilled in the art will readily appreciate, expression of a gene is not sufficient to make it a good vaccine candidate. The only way to determine if a protein is recognized by the immune system during latent infection with *M. tuberculosis* is to produce the given protein and test it in an appropriate assay as described herein. In this regard, our group has demonstrated that antigens strongly expressed by mycobacteria, such as ESAT-6 (Early Secretory Antigen Target-6) are recognized in individuals in all stages of infection and in fact in particular in latently infected individuals (Ravn 1999, Doherty 2002). However the ESAT-6 specific T cells primed during the natural infection are although they may be present in large numbers, almost exclusively of the so called effector phenotype that are terminally differentiated T cells with a very limited lifespan and of low activity as protective T cells against infectious diseases (Seder R, et al. 2008). This is markedly different from the high quality, so called polyfunctional T cells that are promoted by the vaccine demonstrated in the present study to protect against reactivation of TB.

It is far from all highly expressed and immunogenic proteins that are useful as post exposure vaccines because many will provoke hypersensitivity reactions and thereby worsen the situation instead. This was clearly demonstrated in the clinical trial of Koch's original tuberculin vaccine. The vaccine was given as a post exposure vaccine to patients suffering from different forms of the disease including skin and pulmonary TB. The trial was a complete failure and several of the enrolled patients died because of severe hypersensitive reactions (Guttstadt A. 1891). Of the several hundred antigens known to be expressed during primary infection, and tested as vaccines, less than a half dozen have demonstrated significant potential. So far only one antigen has been shown to have any potential as a post exposure vaccine (Lowrie, 1999). However this vaccine only worked if given as a DNA vaccine, an experimental technique so far not approved for use in humans. Moreover, the technique has proved controversial, with other groups claiming that vaccination using this protocol induces either non-specific protection or even worsens disease (Turner, 2000).

Therefore, an effective postexposure vaccination strategy to protect infected individuals against reactivation of the disease is highly desirable.

SUMMARY OF THE INVENTION

The invention is related to treating infections caused by species of the tuberculosis complex (*Mycobacterium tuberculosis, M. Bovis, M. africanum*) by a vaccine that can be administered to latently infected individuals to prevent reactivation of latent tuberculosis infection caused by species of the tuberculosis complex microorganisms (*Mycobacterium tuberculosis., M. bovis, M. africanum*), by targeting constitutively expressed antigens such as ESAT6, CFP10 and EspA. ESAT6, CFP10 and EspA are all interdependently required for secretion and all belong to the ESX-1 secretion system known to be essential for virulence. These secreted antigens are crucial for bacterial dessimination and lysis of cellular membranes. ESAT6, CFP10 and EspA are also antigens that are constitutively expressed in the different stages of disease—whereas, e.g., the expression of Ag85 is downregulated shortly after infection. Surprisingly immunogenic constitutively expressed antigens are preventing reactivation of latent tuberculosis infection when administered as a post exposure vaccine thereby keeping the infection latent.

DETAILED DISCLOSURE OF THE INVENTION

The invention discloses a vaccine or immunogenic composition that is administered post-exposure to latently infected individuals that prevents reactivation of tuberculosis comprising an antigen which is constitutively expressed during infection with *M. tuberculosis* or a nucleic acid encoding said antigen.

Preferably the composition comprises constitutively expressed antigens belonging to the ESX-1 secretion system, ESAT6 (SEQ ID NO. 1), CFP10 (SEQ ID NO. 2), EspA (SEQ ID NO.3), Rv3614c (SEQ ID NO. 4), Rv3615c (SEQ ID NO. 5), EspR (SEQ ID NO. 6), Rv3868 (SEQ ID NO. 7) Rv3869 (SEQ ID NO. 8), Rv3870 (SEQ ID NO. 9), Rv3871 (SEQ ID NO. 10), Rv3872 (SEQ ID NO. 11), Rv3873 (SEQ ID NO. 12), Rv3876 (SEQ ID NO. 13), Rv3877 (SEQ ID NO. 14), Rv3878 (SEQ ID NO. 15), Rv3879c (SEQ ID NO. 16), Rv3880c (SEQ ID NO. 17), Rv3881c (SEQ ID NO. 18), Rv3882c (SEQ ID NO 32), Rv3883c (SEQ ID NO 33), Rv3865c (SEQ ID NO 34) or an immunogenic portion, e.g. a T-cell epitope, of any one of these sequences or an amino acid sequence analogue having at least 70% sequence identity to any one of the sequences in and at the same time being immunogenic.

Alternatively the composition comprises a mix of immunogenic portions preferably selected from the group consisting of SEQ ID NO. 19, 20, 21, 22, 23, 24, 25, 26, 27, 28, 29, 30 and 31.

Another embodiment of the invention is a composition where said polypeptides are fused to an antigen expressed by bacteria within the mycobacteria family preferably where the fusion partner is an antigen which is constitutively expressed. A preferred fusion protein comprises ESAT6 fused to CFP10.

The composition according to the invention preferably comprises an additional delivery system selected among, live recombinant vaccines, that is gene-modified organisms such as bacteria or viruses expressing mycobacterial genes, or immunogenic delivery systems such as, DNA vaccines, that is plasmids expressing genes or gene fragments for the proteins described above, or protein vaccines, that is the proteins themselves or synthetic peptides derived from the proteins themselves delivered in a delivery system such as an adjuvant. The adjuvant is preferably selected from the group consisting of dimethyldioctadecylammonium bromide (DDA), Quil A, poly I:C, aluminium hydroxide, Freund's incomplete adjuvant, IFN-γ, IL-2, IL-12, monophosphoryl lipid A (MPL), Trehalose Dimycolate (TDM), Trehalose Dibehenate and muramyl dipeptide (MDP) most preferably an adjuvant promoting a polyfunctional T-cell response such as DDA/TDB and IC31. The most preferred adjuvant comprises DDA/TDB and/or poly I:C. Alternatively the amino acid sequence is lipidated so as to allow a self-adjuvanting effect of the polypeptide.

The invention also discloses antigens described above for use in treatment of latent tuberculosis and preventing reactivation of the infection.

A method for treating an animal, including a human being, against reactivation of the tuberculosis infection caused by virulent mycobacteria, e.g. by *Mycobacterium tuberculosis, Mycobacterium africanum* or *Mycobacterium bovis*, comprising administering to the animal the vaccine or immunogenic composition described above, wherein said vaccine or immunogenic composition is administered post infection, such as during or after acute stage infection and/or during latent stage infection.

The method can comprise a step of identifying a subject latently infected with a virulent mycobacteria e.g. by a diagnostic procedure such as the Mantoux tuberculin skin test (TST), the Quantiferon test, in vitro detection of responses to HBHA or the detection of IP10 after stimulation with a constitutively expressed antigen.

The invention also discloses the use of an antigen described above for the manufacture of a postexposure vaccine or immunogenic composition against reactivation of latent infections caused by species of the tuberculosis complex e.g. *Mycobacterium tuberculosis, M. bovis* and *M. africanum*, wherein said vaccine or immunogenic composition is for administration post infection, such as during or after acute stage infection and/or during latent stage comprising one or more immunogenic portions described above.

*Mycobacterium*'s success as a pathogen is due to the complex and delicate way it interacts with its host—a process controlled in part by the specialized ESX-1 bacterial protein-secretion system. The ESX-1 system delivers bacterial proteins (e.g. ESAT-6, CFP10 and EspA) into host cells and is critical for virulence. After being secreted from the bacilli the ESAT-6 proteins forms pores in the phagosomal membrane, allowing the bacilli to escape into the cytosol from its containment in the phagosome and thereby it facilitates cell-to-cell spread.

The constitutive expression pattern is an important feature that illustrates that these molecules fulfill essential functions of crucial importance for the pathogen, functions that depend upon genes that need to be constitutively expressed for the pathogen to survive in the immune host. These molecules are the basis for the current invention and are particularly important antigens for vaccines administered to latently infected individuals as they target all stages of the bacterial lifestyle and therefore has the broadest possible basis for activity.

ESAT6, CFP10 and EspA are all interdependently required for secretion and all belong to the ESX-1 secretion system known to be essential for virulence. These secreted antigens are crucial for bacterial dissemination and lysis of cellular membranes. ESAT6, CFP10 and EspA are also antigens that are constitutively expressed in the different stages of disease—whereas e.g. the expression of Ag85 is downregulated shortly after infection. Immunogenic constitutively expressed antigens prevent reactivation of latent tuberculosis infection when administered as a therapeutic vaccine thereby keeping the infection latent.

DEFINITIONS

Polyfunctional T Cells

By the term Polyfunctional T cells is understood T cells that simultaneously express all the cytokines IFN-γ, IL-2, and TNF-α, or IL-2 plus at least one of the two other cytokines IFN-γ and TNF-α.

Polypeptides

The word "polypeptide" in the present invention should have its usual meaning. That is an amino acid chain of any length, including a full-length protein, oligopeptides, short peptides and fragments thereof, wherein the amino acid residues are linked by covalent peptide bonds.

The polypeptide may be chemically modified by being glycosylated, by being lipidated (e.g. by chemical lipidation with palmitoyloxy succinimide as described by Mowat et al. 1991 or with dodecanoyl chloride as described by Lustig et al. 1976), by comprising prosthetic groups, or by containing additional amino acids such as e.g. a his-tag or a signal peptide.

Each polypeptide may thus be characterized by specific amino acids and be encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and still be immunogenic in any of the biological assays described herein. Substitutions are preferably "conservative". These are defined according to the following table. Amino acids in the same block in the second column and preferably in the same line in the third column may be substituted for each other. The amino acids in the third column are indicated in one-letter code.

| ALIPHATIC | Non-polar | GAP |
| --- | --- | --- |
| | | ILV |
| | Polar-uncharged | CSTM |
| | | NQ |
| | Polar-charged | DE |
| | | KR |
| AROMATIC | | HFWY |

A preferred polypeptide within the present invention is an immunogenic antigen from *M. tuberculosis* produced when the organism is subjected to the stresses associated with latent infection. Such antigen can for example also be derived from the *M. tuberculosis* cell and/or *M. tuberculosis* culture filtrate. Thus, a polypeptide comprising an immunogenic portion of one of the above antigens may consist entirely of the immunogenic portion, or may contain additional sequences. The additional sequences may be derived from the native *M. tuberculosis* antigen or be heterologous and such sequences may, but need not, be immunogenic.

Each polypeptide is encoded by a specific nucleic acid sequence. It will be understood that such sequences include analogues and variants hereof wherein such nucleic acid sequences have been modified by substitution, insertion, addition or deletion of one or more nucleic acid. Substitutions are preferably silent substitutions in the codon usage which will not lead to any change in the amino acid sequence, but may be introduced to enhance the expression of the protein.

In the present context the term "substantially pure polypeptide fragment" means a polypeptide preparation which contains at most 5% by weight of other polypeptide material with which it is natively associated (lower percentages of other polypeptide material are preferred, e.g. at most 4%, at most 3%, at most 2%, at most 1%, and at most ½%). It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99.25%, at least 99.5%, and at least 99.75%. It is especially preferred that the polypeptide fragment is in "essentially pure form", i.e. that the polypeptide fragment is essentially free of any other antigen with which it is natively associated, i.e. free of any other antigen from bacteria belonging to the tuberculosis complex or a virulent *mycobacterium*. This can be accomplished by preparing the polypeptide fragment by means of recombinant methods in a non-mycobacterial host cell as will be described in detail below, or by synthesizing the polypeptide fragment by the well-known methods of solid or liquid phase peptide synthesis, e.g. by the method described by Merrifield (Merrifield 1963) or variations thereof. For the purpose of the present invention it will be understood that the above definition of "substantially pure polypeptide or polypeptide fragment" does not exclude such polypeptides or polypeptide fragments when present in combination with other purified or synthetic antigens of mycobacterial or non-mycobacterial origin.

By the term "virulent *mycobacterium*" is understood a bacterium capable of causing the tuberculosis disease in an animal or in a human being. Examples of virulent mycobacteria include but are not limited to *M. tuberculosis, M. africanum*, and *M. bovis*. Examples of relevant animals are cattle, possums, badgers and kangaroos.

By "an infected individual" is understood an individual with culture or microscopically proven infection with virulent mycobacteria, and/or an individual clinically diagnosed with TB and who is responsive to anti-TB chemotherapy. Culture, microscopy and clinical diagnosis of TB are well known by any person skilled in the art.

By the term "PPD-positive individual" is understood an individual with a positive Mantoux test or an individual where PPD (purified protein derivative) induces a positive in vitro recall response determined by release of IFN-γ.

By "a latently infected individual" is understood an individual, who has been infected by a virulent *mycobacterium*, e.g. *M. tuberculosis*, but shows no sign of active tuberculosis. It is likely that individuals who have been vaccinated, e.g. by BCG, or treated for TB may still retain the mycobacteria within their bodies, although this is currently impossible to prove since such individuals would be expected to be positive if tested for PPD reactivity. Nonetheless, in its most accurate sense, "latently-infected" may be used to describe any individual who has *M. tuberculosis* residing in their tissues but who is not clinically ill. A latently infected individual can be identified by a number of methods in clinical use today such as the Mantoux tuberculin skin test (TST), the Quantiferon test and in the future there may be even more sensitive means of diagnosing this particular stage of the infection such as the recently suggested in vitro detection of responses to HBHA (Hougardy 2007) or the detection of IP10 after stimulation in vitro with ESAT6 (Ruhwald 2008)

By the term "reactivation" is understood the situation where the balance between non-replicating bacteria (that may be very difficult for the immune system to detect as they are located intracellularly) and slowly replicating bacteria that has an active but changed expression profile in an attempt to adapt to the hostile environment encountered in the immune host is tilted in favour of the pathogen and the infection goes into the phase, where the bacteria start replicating rapidly again and bacterial numbers in the infected individual increases. These bacteria that replicate in latently infected individuals under very strong immune pressure are the target for the vaccination strategy in the present invention.

By the term "IFN-γ" is understood interferon-gamma. The measurement of IFN-γ is used as an indication of an immunological response.

By the terms "nucleic acid fragment" and "nucleic acid sequence" are understood any nucleic acid molecule including DNA, RNA, LNA (locked nucleic acids), PNA, RNA, dsRNA and RNA-DNA-hybrids. Also included are nucleic acid molecules comprising non-naturally occurring nucleosides. The term includes nucleic acid molecules of any length e.g. from 10 to 10000 nucleotides, depending on the use. When the nucleic acid molecule is for use as a pharmaceutical, e.g. in DNA therapy, or for use in a method for producing a polypeptide according to the invention, a molecule encoding at least one epitope is preferably used, having a length from about 18 to about 1000 nucleotides, the molecule being optionally inserted into a vector.

Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

Constitutively expressed genes are defined as genes that after a detailed analysis of mRNA at a population level are equally well expressed in vivo in the lung at time points later than three weeks post infection after being correlated for M. tb. CFU numbers in the lung. From this definition it follows that a constitutive gene may be differentially expressed at a single bacteria level. The method to quantitate gene expression is quantitative PCR. "Equally well" is defined as being within +/−5 fold the level from the previous measurement The comparison is always to the time point immediately preceding the current. Time between measurements cannot be longer than the time between infection and the previous measurement. E.g. if expression of a gene is measured the first time at week 3 post infection the second measurement can not be done later than 6 weeks post infection and the third 12 weeks post infection etc.

Constitutively expressed antigens are polypeptides or part of these polypeptides which are products of constitutively expressed genes.

Sequence Identity

The term "sequence identity" indicates a quantitative measure of the degree of homology between two amino acid sequences of equal length or between two nucleotide sequences of equal length. The two sequences to be compared must be aligned to best possible fit allowing the insertion of gaps or alternatively, truncation at the ends of the protein sequences. The sequence identity can be calculated as $$\frac{(N_{ref} - N_{dif})100}{N_{ref}},$$

wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$). Sequence identity can alternatively be calculated by the BLAST program e.g. the BLASTP program (Pearson, 1988, or www.ncbi.nlm.nih.gov/cgi-bin/BLAST). In one aspect of the invention, alignment is performed with the sequence alignment method ClustalW with default parameters as described by Thompson J., et al 1994.

A preferred minimum percentage of sequence identity is at least 80%, such as at least 85%, at least 90%, at least 91%, at least 92%, at least 93%, at least 94%, at least 95%, at least 96%, at least 97%, at least 98%, at least 99%, and at least 99.5%.

Immunogenic Portion

In a preferred embodiment of the invention, the polypeptide comprises an immunogenic portion of the polypeptide, such as an epitope for a B-cell or T-cell.

The immunogenic portion of a polypeptide is a part of the polypeptide, which elicits an immune response in an animal or a human being, and/or in a biological sample determined by any of the biological assays described herein. The immunogenic portion of a polypeptide may be a T-cell epitope or a B-cell epitope. Immunogenic portions can be related to one or a few relatively small parts of the polypeptide, they can be scattered throughout the polypeptide sequence or be situated in specific parts of the polypeptide. For a few polypeptides epitopes have even been demonstrated to be scattered throughout the polypeptide covering the full sequence (Ravn et al 1999). In order to identify relevant T-cell epitopes which are recognised during an immune response, it is possible to use overlapping oligopeptides for the detection of MHC class II epitopes, preferably synthetic, having a length of e.g. 20 amino acid residues derived from the polypeptide. These peptides can be tested in biological assays (e.g. the IFN-γ assay as described herein) and some of these will give a positive response (and thereby be immunogenic) as evidence for the presence of a T cell epitope in the peptide. For ESAT-6 and CFP10 such studies have shown that every part of the antigen contains T-cell epitopes (Mustafa et al. 2000, Arend S M et al. 2000). For the detection of MHC class I epitopes it is possible to predict peptides that will bind (Stryhn et al. 1996) and hereafter produce these peptides synthetic and test them in relevant biological assays e.g. the IFN-γ assay as described herein. The peptides preferably having a length of e.g. 8 to 11 amino acid residues derived from the polypeptide. B-cell epitopes can be determined by analysing the B cell recognition to overlapping peptides covering the polypeptide of interest as e.g. described in Harboe et al 1998. Consistent with this definition, an immunogenic portion of a polypeptide as described herein can be identified as a portion which elicits an immune response, c.f. the definition of "immune response" herein below.

Although the minimum length of a T-cell epitope has been shown to be at least 6 amino acids, it is normal that such epitopes are constituted of longer stretches of amino acids. Hence, it is preferred that the polypeptide fragment of the invention has a length of at least 7 amino acid residues, such as at least 8, at least 9, at least 10, at least 12, at least 14, at least 16, at least 18, at least 20, at least 22, at least 24, and at least 30 amino acid residues. Hence, in important embodiments of the inventive method, it is preferred that the polypeptide fragment has a length of at most 50 amino acid residues, such as at most 40, 35, 30, 25, and 20 amino acid residues. It is expected that the peptides having a length of between 10 and 20 amino acid residues will prove to be most efficient as MHC class II epitopes and therefore especially preferred lengths of the polypeptide fragment used in the inventive method are 18, such as 15, 14, 13, 12 and even 11 amino acid residues. It is expected that the peptides having a length of between 7 and 12 amino acid residues will prove to be most efficient as MHC class I epitopes and therefore especially preferred lengths of the polypeptide fragment used in the inventive method are 11, such as 10, 9, 8 and even 7 amino acid residues.

Immunogenic portions of polypeptides may be recognised by a broad part (high frequency) or by a minor part (low frequency) of the genetically heterogeneous human population. In addition some immunogenic portions induce high immunological responses (dominant), whereas others induce lower, but still significant, responses (subdominant). High frequency><low frequency can be related to the immunogenic portion binding to widely distributed MHC molecules (HLA type) or even by multiple MHC molecules (Sinigaglia, 1988, Kilgus, 1991).

In the context of providing candidate molecules for a new vaccine against tuberculosis, the subdominant epitopes are however as relevant as are the dominant epitopes since it has been shown (Olsen, 2000) that such epitopes can induce protection regardless of the fact that they are not as strongly or broadly recognised.

Variants

A common feature of the polypeptides of the invention is their capability to induce an immunological response as illustrated in the examples. It is understood that a variant of a polypeptide of the invention produced by substitution, insertion, addition or deletion may also be immunogenic as determined by any of the assays described herein.

Immune Individual

An immune individual is defined as a person or an animal, which has cleared or controlled an infection with virulent mycobacteria or has received a prophylactic vaccination, such as vaccination with *M. bovis* BCG.

Immune Response

The immune response may be monitored by one of the following methods:

An in vitro cellular response is determined by induction of the release of a relevant cytokine such as IFN-γ from, or the induction of proliferation in lymphocytes withdrawn from an animal or human being currently or previously infected with virulent mycobacteria or immunized with the relevant polypeptide. The induction being performed by the addition of the polypeptide or the immunogenic portion of the polypeptide to a suspension comprising from $2\times10^5$ cells to $4\times10^5$ cells per well. The cells being isolated from either the blood, the spleen, the liver or the lung and the addition of the polypeptide or the immunogenic portion resulting in a concentration of not more than 20 μg per ml suspension and the stimulation being performed from two to five days. For monitoring cell proliferation the cells are pulsed with radioactive labeled Thymidine and after 16-22 hours of incubation detecting the proliferation by liquid scintillation counting. A positive response is defined as being a response more than background plus two standard deviations. The release of IFN-γ can be determined by the ELISA method, which is well known to a person skilled in the art. A positive response being a response more than background plus two standard deviations. Other cytokines than IFN-γ could be relevant when monitoring the immunological response to the polypeptide, such as IL-12, TNF-α, IL-4, IL-5, IL-10, IL-6, TGF-β. Another and more sensitive method for detecting the immune response is the ELISpot method, in which the frequency of IFN-γ producing cells is determined. In an ELIspot plate (MAHA, Millipore) precoated with anti-murine IFN-γ antibodies (PharMingen) graded numbers of cells isolated from either blood, spleen, or lung (typically between 1 to $4\times10^5$ cells/well) are incubated for 24-32 hrs in the presence of the polypeptide or the immunogenic portion resulting in a concentration of not more than 20 µg per ml. The plates are subsequently incubated with biotinylated anti-IFN-γ antibodies followed by a streptavidin-alkaline phosphatase incubation. The IFN-γ producing cells are identified by adding BCIP/NBT (Sigma), the relevant substrate giving rise to spots. These spots can be enumerated using a dissection microscope. It is also a possibility to determine the presence of mRNA coding for the relevant cytokine by the use of the PCR technique. Usually one or more cytokines will be measured utilizing for example PCR, ELISPOT or ELISA. It will be appreciated by a person skilled in the art that a significant increase or decrease in the amount of any of these cytokines induced by a specific polypeptide can be used in evaluation of the immunological activity of the polypeptide.

An in vitro cellular response may also be determined by the use of T cell lines derived from an immune individual or an *M. tuberculosis*-infected person where the T cell lines have been driven with either live mycobacteria, extracts from the bacterial cell or culture filtrate for 10 to 20 days with the addition of IL-2. The induction being performed by addition of not more than 20 µg polypeptide per ml suspension to the T cell lines containing from $1\times10^5$ cells to $3\times10^5$ cells per well and incubation being performed from two to six days. The induction of IFN-γ or release of another relevant cytokine is detected by ELISA. The stimulation of T cells can also be monitored by detecting cell proliferation using radioactively labeled Thymidine as described above. For both assays a positive response being a response more than background plus two standard deviations.

An in vivo cellular response may be determined as a positive DTH response after intradermal injection or local application patch of at most 100 µg of the polypeptide or the immunogenic portion to an individual who is clinically or subclinically infected with a virulent mycobacterium, a positive response having a diameter of at least 5 mm 72-96 hours after the injection or application.

An in vitro humoral response is determined by a specific antibody response in an immune or infected individual. The presence of antibodies may be determined by an ELISA technique or a Western blot where the polypeptide or the immunogenic portion is absorbed to either a nitrocellulose membrane or a polystyrene surface. The serum is preferably diluted in PBS from 1:10 to 1:100 and added to the absorbed polypeptide and the incubation being performed from 1 to 12 hours. By the use of labeled secondary antibodies the presence of specific antibodies can be determined by measuring the OD e.g. by ELISA where a positive response is a response of more than background plus two standard deviations or alternatively a visual response in a Western blot.

Another relevant parameter is measurement of the protection in animal models induced after vaccination with the polypeptide in an adjuvant or after DNA vaccination. Suitable animal models include primates, guinea pigs or mice, which are challenged with an infection of a virulent *Mycobacterium*. Readout for induced protection could be decrease of the bacterial load in target organs compared to non-vaccinated animals, prolonged survival times compared to non-vaccinated animals and diminished weight loss compared to non-vaccinated animals.

Preparation Methods

In general, *M. tuberculosis* antigens, and DNA sequences encoding such antigens, may be prepared using any one of a variety of procedures.

They may be purified as native proteins from the *M. tuberculosis* cell or culture filtrate by procedures such as those described above. Immunogenic antigens may also be produced recombinantly using a DNA sequence encoding the antigen, which has been inserted into an expression vector and expressed in an appropriate host. Examples of host cells are *E. coli*. The polypeptides or immunogenic portion hereof can also be produced synthetically having fewer than about 100 amino acids, and generally fewer than 50 amino acids and may be generated using techniques well known to those ordinarily skilled in the art, such as commercially available solid-phase techniques where amino acids are sequentially added to a growing amino acid chain.

In the construction and preparation of plasmid DNA encoding the polypeptide as defined for DNA vaccination a host strain such as *E. coli* can be used. Plasmid DNA can then be prepared from cultures of the host strain carrying the plasmid of interest, and purified using e.g. the Qiagen Giga-Plasmid column kit (Qiagen, Santa Clarita, Calif., USA) including an endotoxin removal step. It is preferred that plasmid DNA used for DNA vaccination is endotoxin free.

Fusion Proteins

The immunogenic polypeptides may also be produced as fusion proteins, by which methods superior characteristics of the polypeptide of the invention can be achieved. For instance, fusion partners that facilitate export of the polypeptide when produced recombinantly, fusion partners that facilitate purification of the polypeptide, and fusion partners which enhance the immuno-genicity of the polypeptide fragment of the invention are all interesting possibilities. Therefore, the invention also pertains to a fusion polypeptide comprising at least one polypeptide or immunogenic portion defined above and at least one fusion partner. The fusion partner can, in order to enhance immunogenicity, be another polypeptide derived from *M. tuberculosis*, such as of a polypeptide fragment derived from a bacterium belonging to the tuberculosis complex, such as ESAT-6, CFP10, EspA, TB10.4, RD1-ORF5, RD1-ORF2, Rv1036, MPB64, MPT64, Ag85A, Ag85B (MPT59), MPB59, Ag85C, 19 kDa lipoprotein, MPT32 and alpha-crystallin, or at least one T-cell epitope of any of the above mentioned antigens (Skjøt et al 2000; WO0179274; WO0104151; U.S. patent application Ser. No. 09/505,739; Rosenkrands et al 1998; Nagai et al 1991). The invention also pertains to a fusion polypeptide comprising mutual fusions of two or more of the polypeptides (or immunogenic portions thereof) of the invention. Other fusion partners, which could enhance the immunogenicity of the product, are lymphokines such as IFN-γ, IL-2 and IL-12. In order to facilitate expression and/or purification, the fusion partner can e.g. be a bacterial fimbrial protein, e.g. the pilus components pilin and papA; protein A; the ZZ-peptide (ZZ-fusions are marketed by Pharmacia in Sweden); the maltose binding protein; glutathione S-transferase; β-galactosidase; or polyhistidine. Fusion proteins can be produced recombinantly in a host cell, which could be *E. coli*, and it is a possibility to induce a linker region between the different fusion partners.

Other interesting fusion partners are polypeptides, which are lipidated so that the immunogenic polypeptide is presented in a suitable manner to the immune system. This effect is e.g. known from vaccines based on the *Borrelia burgdorferi* OspA polypeptide as described in e.g. WO 96/40718 A or vaccines based on the *Pseudomonas aeruginosa* OprI lipoprotein (Cote-Sierra J 1998). Another possibility is N-terminal fusion of a known signal sequence and an N-terminal cystein to the immunogenic polypeptide. Such a fusion results in lipidation of the immunogenic polypeptide at the N-terminal cystein, when produced in a suitable production host.

Uses

Vaccine

A vaccine is a biological preparation that establishes or improves immunity to a particular disease. Vaccines can be prophylactic (e.g. to prevent or ameliorate the effects of a future infection by any natural or "wild" pathogen), postexposure (e.g. to prevent reactivation in latently infected individuals without clinical symptoms) or therapeutic (e.g. vaccines used to treat active disease either alone or combined with antibiotic treatment to shorten treatment)

An Animal Model for Latent TB

To induce a low grade latent infection with M. tb., animals are first given an aerosol infection using a normal dose of M.tb (approximately 150 bacteria in the lungs). After 6 weeks of infection, the animals are then given a suboptimal chemotherapy treatment of 6 weeks during which most—but not all—of the bacteria are eradicated. The remaining bacteria will establish a latent infection. Following the chemotherapy treatment some animals will be vaccinated to examine the ability of the vaccine to prevent re-activation of the latent infection, which will occur spontaneously 5-15 weeks after the chemotherapy treatment. See FIG. 2.

Protein Vaccine

Another part of the invention pertains to a vaccine composition comprising a polypeptide (or at least one immunogenic portion thereof) or fusion polypeptide according to the invention. In order to ensure optimum performance of such a vaccine composition it is preferred that it comprises an immunologically and pharmaceutically acceptable carrier, vehicle or adjuvant.

An effective vaccine, wherein a polypeptide of the invention is recognized by the animal, will in an animal model be able to decrease bacterial load in target organs, prolong survival times and/or diminish weight loss after challenge with a virulent *Mycobacterium*, compared to non-vaccinated animals Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of dimethyldioctadecylammonium bromide (DDA), Quil A, poly I:C, aluminium hydroxide, Freund's incomplete adjuvant, IFN-γ, IL-2, IL-12, monophosphoryl lipid A (MPL), Trehalose Dimycolate (TDM), Trehalose Dibehenate and muramyl dipeptide (MDP).

Preparation of vaccines which contain peptide sequences as active ingredients is generally well understood in the art, as exemplified by U.S. Pat. Nos. 4,608,251; 4,601,903; 4,599,231 and 4,599,230, all incorporated herein by reference.

Other methods of achieving adjuvant effect for the vaccine include use of agents such as aluminum hydroxide or phosphate (alum), synthetic polymers of sugars (Carbopol), aggregation of the protein in the vaccine by heat treatment, aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Other possibilities involve the use of immune modulating substances such as cytokines or synthetic IFN-γ inducers such as poly I:C in combination with the above-mentioned adjuvants.

Another interesting possibility for achieving adjuvant effect is to employ the technique described in Gosselin et al., 1992 (which is hereby incorporated by reference herein). In brief, a relevant antigen such as an antigen of the present invention can be conjugated to an antibody (or antigen binding antibody fragment) against the Fcγ receptors on monocytes/macrophages.

The vaccines are administered in a manner compatible with the dosage formulation, and in such amount as will be immunogenic and effective in preventing re-activation. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 μg to 1000 μg, such as in the range from about 1 μg to 300 μg, and especially in the range from about 10 μg to 50 μg. Suitable regimens for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

The vaccines are conventionally administered intra pulmonary, e.g by aerosol or inhalation, parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95% of active ingredient, preferably 25-70%.

In many instances, it will be necessary to have multiple administrations of the vaccine. In instances where the individual has already become infected or is suspected to have become infected, the previous vaccination may have provided sufficient immunity to prevent primary disease, but as discussed previously, boosting this immune response will not help against the latent infection. In such a situation, the vaccine will necessarily have to be a post exposure vaccine designed for efficacy against the latent stage of infection or re-emerging active tuberculosis infection.

Due to genetic variation, different individuals may react with immune responses of varying strength to the same polypeptide. Therefore, the vaccine according to the invention may comprise several different polypeptides in order to increase the immune response. The vaccine may comprise two or more polypeptides or immunogenic portions, where all of the polypeptides are as defined above, or some but not all of the peptides may be derived from virulent mycobacteria. In the latter example, the polypeptides not necessarily fulfilling the criteria set forth above for polypeptides may either act due to their own immunogenicity or merely act as adjuvants.

The vaccine may comprise 1-20, such as 2-20 or even 3-20 different polypeptides or fusion polypeptides, such as 3-10 different polypeptides or fusion polypeptides.

DNA Vaccine.

The nucleic acid fragments of the invention may be used for effecting in vivo expression of antigens, i.e. the nucleic acid fragments may be used in so-called DNA vaccines as reviewed in Ulmer et al 1993, which is included by reference.

Hence, the invention also relates to a post exposure vaccine comprising a nucleic acid fragment according to the invention, the vaccine effecting in vivo expression of antigen by an animal, including a human being, to whom the vaccine has been administered, the amount of expressed antigen being effective to confer treatment of the infections caused by virulent mycobacteria in an animal, including a human being.

The efficacy of such a DNA vaccine can possibly be enhanced by administering the gene encoding the expression product together with a DNA fragment encoding a polypeptide which has the capability of modulating an immune response.

Live Recombinant Vaccines

One possibility for effectively activating a cellular immune response for a post exposure vaccine can be achieved by expressing the relevant antigen in a vaccine in a non-pathogenic microorganism or virus. Well-known examples of such microorganisms are *Mycobacterium bovis* BCG, *Salmonella* and *Pseudomona* and examples of viruses are Vaccinia Virus and Adenovirus.

Therefore, another important aspect of the present invention is an improvement of the living BCG vaccine presently available, wherein one or more copies of a DNA sequence encoding one or more polypeptide as defined above has been incorporated into the genome of the micro-organism in a manner allowing the micro-organism to express and secrete the polypeptide. The incorporation of more than one copy of a nucleotide sequence of the invention is contemplated to enhance the immune response.

Another possibility is to integrate the DNA encoding the polypeptide according to the invention in an attenuated virus such as the vaccinia virus or Adenovirus (Rolph et al 1997). The recombinant vaccinia virus is able to replicate within the cytoplasma of the infected host cell and the polypeptide of interest can therefore induce an immune response, which is envisioned to induce protection against TB.

All patent and non-patent references cited in the present application, are hereby incorporated by reference in their entirety. The invention will now be described in further details in the following non-limiting examples.

FIGURE LEGENDS

Figure 2:
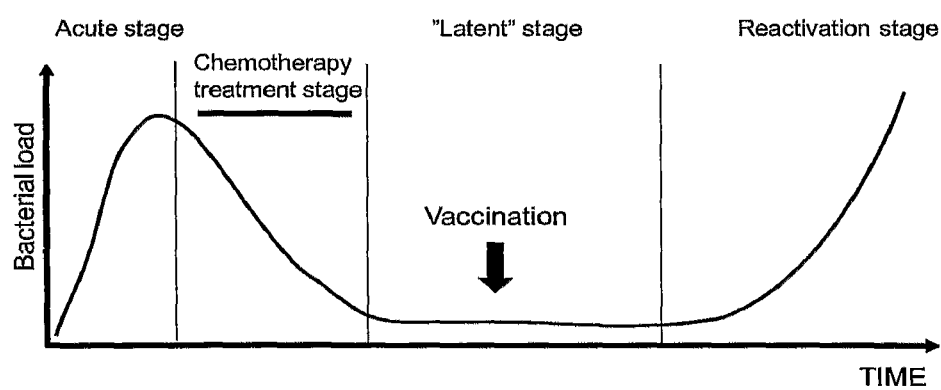

FIG. 1: The course of a *M. tuberculosis* infection runs essentially through 3 phases FIG. 2: Model for postexposure vaccination to prevent reactivation FIG. 3: TB vaccination model.

A schematic overview of the model used at the SSI for the testing of postexposure vaccines. Mice are infected with virulent M.tb by the aerosol route. From weeks 6 to week 12 post infection mice are treated with antibiotics to establish a state of latent TB. The mice are vaccinated 2 to three times with 3 weeks interval initiated at week 10 post infection with the postexposure vaccine candidates. The mice are allowed time to reactivate the disease and approximately 20 weeks later the lungs are assessed for bacterial numbers to assess the protective efficacy of the vaccine.

Figure 4:
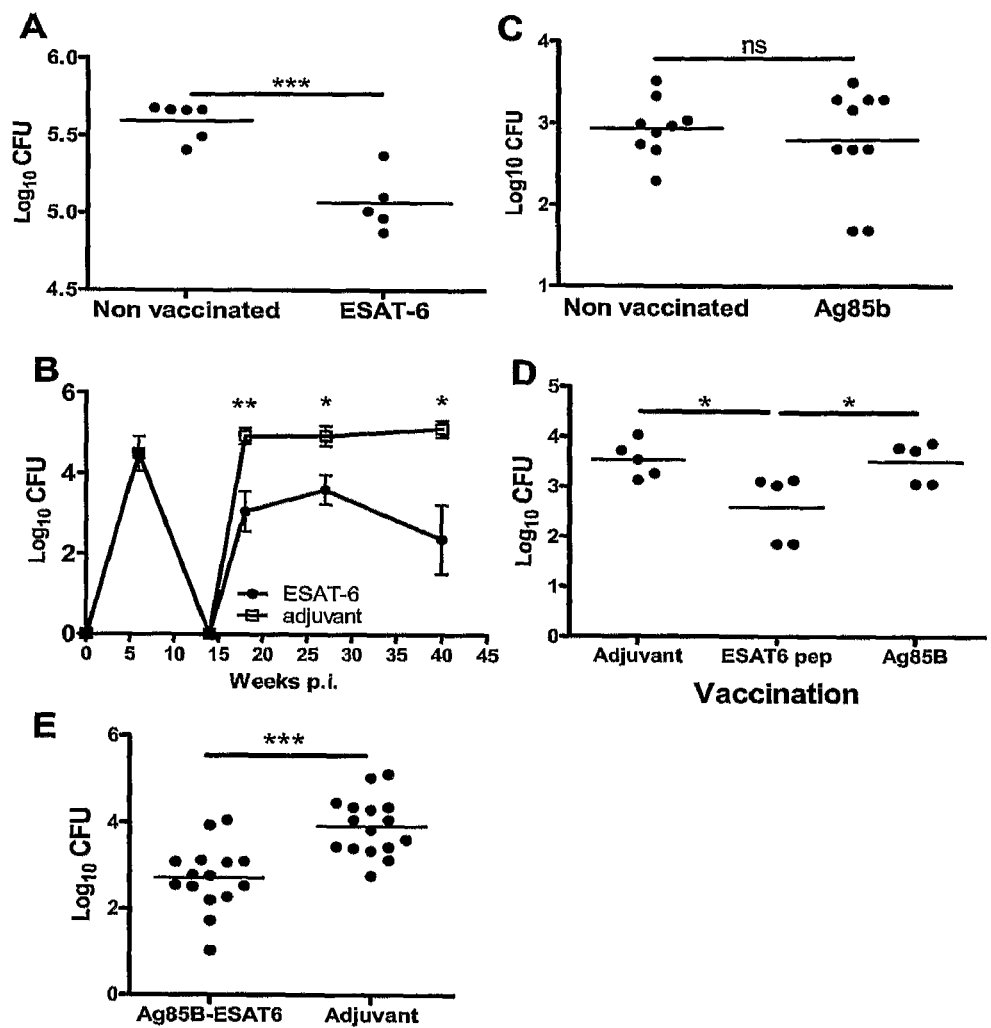

FIG. 4: Post-exposure vaccine induced protection by ESAT6 but not Ag85.

Mice were infected, treated and vaccinated according to the schematic overview in example 1. Mice were killed between week 30-40 post infection and at this timepoint lungs were assessed for bacterial load (FIG. A, C-E) or as displayed in FIG. 4B where the bacterial load was determined at several timepoints throughout infection for ESAT6. (A and B) Bacterial load of ESAT6 vaccinated compared to control animals. (C) Bacterial load of Ag85B vaccinated compared to control animals. (D) Bacterial of ESAT-6 pepmix vaccinated (pool of overlapping peptides covering the entire ESAT6 sequence) compared to both Ag85B vaccinated and control animals. (E) Protection against reactivation following postexposure vaccination with Ag85B-ESAT-6 (H1) vaccinated compared to non-vaccinated control mice. All data in FIG. 4A, C-E are displayed as dot plots representing each individual animal with the mean depicted whereas each timepoint in FIG. 4B is representative of 6 individual animals and displayed as mean±standard error of the mean (SEM) (B). All statistical analyses were performed using either an unpaired t-test (FIGS. A-C and E) or Tukey's multiple comparison test (FIG. D) where p<0.05 was considered significant.

Figure 5:
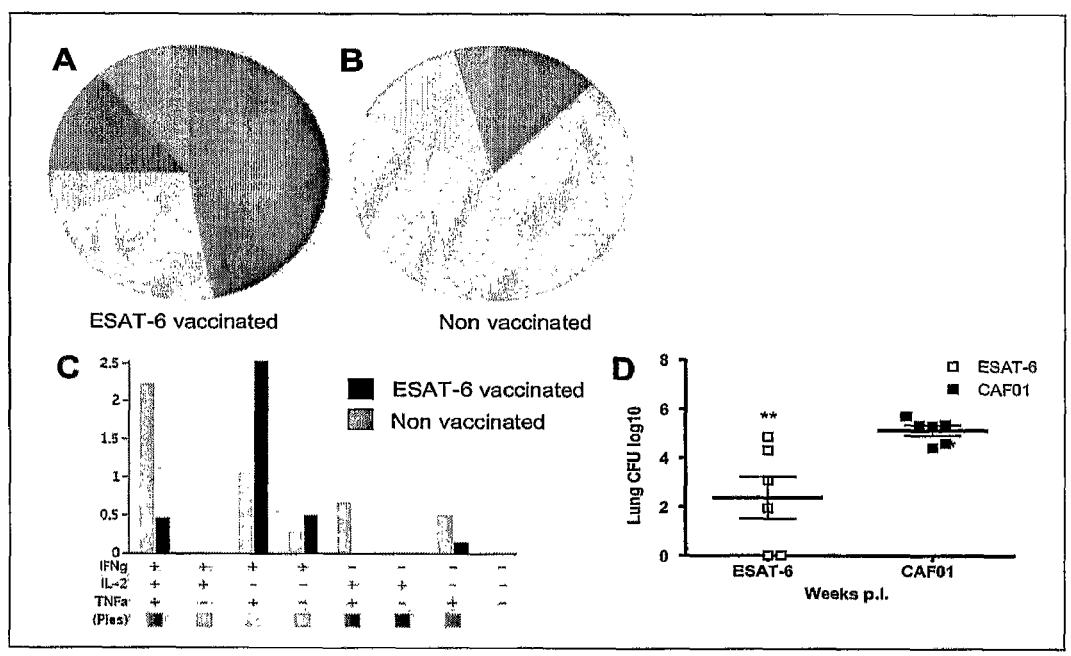

FIG. 5: ESAT-6 postexposure vaccination induce polyfunctional T cells.

Cells from infected lungs from non-vaccinated or ESAT-6 vaccinated animals were stimulated in vitro with ESAT-6 prior to staining with anti-CD4, -CD8, -IFN-$\gamma$, -TNF-$\alpha$ and -IL-2. (A and B) Cytokine profiles were determined by first dividing the CD4 T cells into IFN-$\gamma$ positive (+) or IFN-$\gamma$ negative (−) cells. Both the IFN-$\gamma$+ and IFN-$\gamma$− cells were analyzed with respect to the production of TNF-$\alpha$ and IL-2. The pie charts (A and B) are colour coded according to the cytokine production profile and summarizes the fractions of the CD4$^+$ T cell response (out of the ESAT-6 specific CD4 T cells) that are positive for a given cytokine production profile. (C) Every possible combination of cytokines is shown on the x-axis of the bar chart and the percentage of ESAT-6 specific CD4$^+$ T cells in non vaccinated mice (grey bars) or ESAT-6 vaccinated mice (Black bars) expressing any combination of cytokines is given for each immunization group. D. Latently infected mice were vaccinated twice with ESAT-6, and 20 weeks after the last vaccination, lungs were assessed for bacterial number to determine protective efficacy. (**p<0.01, One way ANOVA Tukey's multiple comparisons test).

Figure 6:
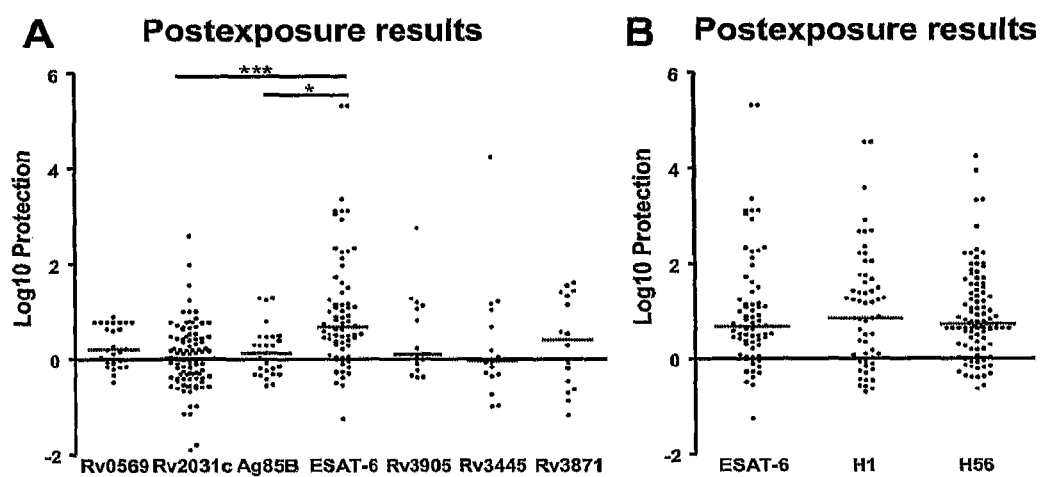

FIG. 6: Pooled analysis of all postexposure experiments

For an individual experiment where either ESAT6, Rv3871, Ag85B, Rv3905, Rv3445, Rv0569 or Rv2031c (FIG. A), Ag85B-ESAT6 (H1) or Ag85B-ESAT6-Rv2660 (H56) (FIG. B) was used for post-exposure vaccination the median of the bacterial load of the adjuvant control group was compared to the bacterial load of each individual mouse in a vaccinated group vaccinated with either one of the antigens mentioned above. In figure A and B each dot corresponds to the level of protection i.e. ΔLog 10 CFU conferred by the vaccination compared to the adjuvant control group and consists of several independent experiments. (A) Log 10 protection for the single antigens ESAT6, Rv3871, Ag85B, Rv3905, Rv3445, Rv0569 or Rv2031c (B) or for the hybrid antigens H1 and H56 compared to ESAT6 alone. A statistical analysis was applied for comparisons of medians between the different groups either using the Kruskall Wallis multiple comparison test. p<0.05 was considered significant.

Figure 7:
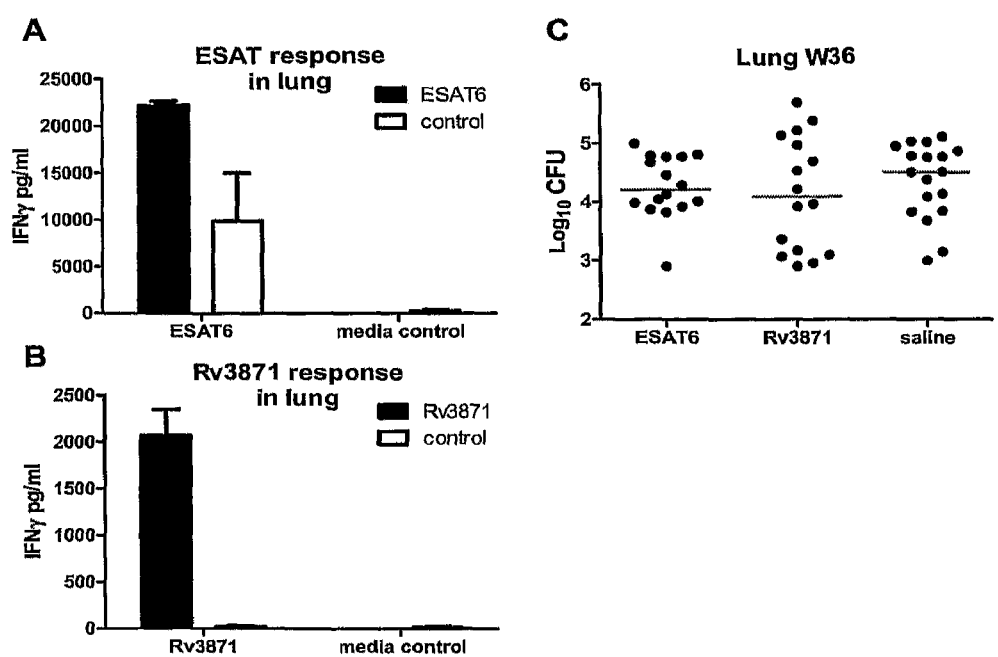

FIG. 7: Effect of postexposure vaccination with Rv3871 compared to ESAT6 and control animals.

Mice were infected, treated and vaccinated at week 10, 13 and 18 post infection. At week 36 post infection the mice were terminated and lung lymphocytes from both vaccinated and non-vaccinated saline control mice were restimulated in vitro with Rv3871 (FIG. 7A) or ESAT6 (FIG. 7B). IFN-γ releases assessed by ELISA and samples were performed in triplicated. Data are depicted as mean±SEM. The protective efficacy conferred by the vaccines was determined by enumeration of bacteria in the lung cultured from full lung homogenate (n=16-18). FIG. 7C shows data displayed as a dot plot where each dot represents an individual animal and depicted with the median (line).

EXAMPLES

Example 1

Murine TB Model for Vaccination

Figure 3:
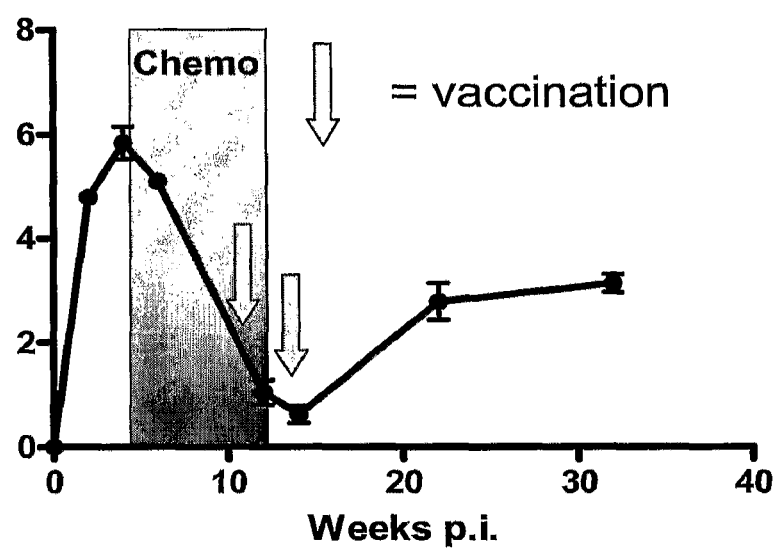

The Cornell model has widely been used as a murine model for the study of latent TB. This model has been adapted in our laboratory for the testing of the ability of vaccine candidates to prevent reactivation. Mice are initially aerosolly infected with virulent M.tb. and at week 6 post infection antibiotic treatment is initiated to reduce the bacterial load. This is to mimic the latent stage of a human infection which does not occur spontaneously in mice. During this latent stage (a stage with continuous low bacterial numbers) the mice are being immunized twice and the ability to prevent reactivation by the vaccine is determined by culturing the spleen and lungs for live M.tb. 20 weeks after the last immunization. The long timespan of the experiments is necessary to allow sufficient time for reactivation of the disease which is a prerequisite for readout of vaccine efficacy (FIG. 3).

Example 2

Postexposure Vaccine Induced Protection by ESAT6 but not Ag85

ESAT-6 and Ag85B have proven to be protective in prophylactic vaccination both as single components and also as the fusion molecule Ag85B-ESAT6 (H1). However, when these antigens were tested in the postexposure model (as described above in example 1) only ESAT6 has a protective effect and control bacteria growth during the reactivation phase (FIG. 4). Furthermore, as seen in FIG. 4B ESAT6 protection against reactivation manifests itself as early as W18 post infection and this protection was maintained throughout the course of the experiment (up until week 40 post infection). This is in contrast to what is observed when Ag85B is used as a post exposure vaccine (FIGS. 4C and D), where there is no significant decrease in bacterial load compared to the control. In addition, we evaluated the H1 fusion protein which is composed of the TB antigens Ag85B and ESAT-6 which has shown promising efficacy in a prophylactic setting. When this molecule was used as a post exposure vaccine in the SSI postexposure model it was able to significantly reduce the bacterial numbers (FIG. 4E).

Example 3

Post Exposure Vaccine Induced Protection by ESAT6 Peptide Mix

As shown in the examples above, the ESAT-6 molecule is very active when given postexposure resulting in a decrease in bacterial load compared to the control group and also compared to Ag85B. Furthermore we have shown that ESAT-6 given as a pool of overlapping peptides instead of a recombinant protein also lead to a better protection against reactivation compared to both the control group and Ag85B demonstrating the strong activity of ESAT6, and ability to function as a post exposure vaccine (FIG. 4D).

Overlapping ESAT-6 peptides (P1-P13) used for protection experiment:

| P1  | MTEQQWNFAGIEAAA | (SEQ ID NO. 19) |
| --- | --- | --- |
| P2  | NFAGIEAAASAIQGN | (SEQ ID NO. 20) |
| P3  | ASAIQGNVTSIHSLL | (SEQ ID NO. 21) |
| P4  | NVTSIHSLLDEGKQS | (SEQ ID NO. 22) |
| P5  | SLLDEGKQSLTKLAA | (SEQ ID NO. 23) |
| P6  | KQSLTKLAAAWGGSG | (SEQ ID NO. 24) |
| P7  | AAWGGSGSEAYQGVQ | (SEQ ID NO. 25) |
| P8  | GSEAYQGVQQKWDAT | (SEQ ID NO. 26) |
| P9  | QQKWDATATELNNAL | (SEQ ID NO. 27) |
| P10 | TATELNNALQNLART | (SEQ ID NO. 28) |
| P11 | ALQNLARTISEAGQA | (SEQ ID NO. 29) |
| P12 | TISEAGQAMASTEGN | (SEQ ID NO. 30) |
| P13 | QAMASTEGNVTGMFA | (SEQ ID NO. 31) |

Example 5

Post Exposure Vaccination with ESAT-6 Induce Polyfunctional T Cells

To examine the effect of a post exposure vaccination with ESAT-6 on the cytokine expression profile of the ESAT-6 specific cells, mice were first aerosolly infected with virulent M.tb. and at week 6 post infection antibiotic treatment was initiated to reduce the bacterial load and establish a latent infection. During the latent stage the mice were vaccinated (as shown in FIG. 3) three times with 3 weeks interval and the ability of the ESAT-6 vaccine influence the number of polyfunctional T cells and to prevent reactivation of M.tb was determined 20 weeks after the last vaccination. The results showed that there was a substantial ESAT-6 response in the non-vaccinated group, but the cytokine expression profile was markedly different compared to the ESAT-6 vaccinated group (FIG. 5), in particularly in terms of polyfunctional T cells (IFN-γ+TNF-α+IL-2+ CD4 T cells). Thus, compared to the non vaccinated group, we observed decreased numbers of IFN-γ/TNF-α CD4 T cells, and increased numbers of triple positive polyfunctional CD4 T cells co-expressing IFN-γ/TNF-α/IL-2. The increased presence of polyfunctional T cells correlated with decreased bacterial numbers in the lungs of ESAT-6 vaccinated animals (FIG. 5D).

Example 6

Post-exposure vaccination with ESAT6 more consistently protects against reactivation compared to other antigens associated with both early and late stage infection.

To determine which antigens most consistently protect against reactivation we made a pooled analysis of normalized data based on all post-exposure experiments conducted. Data sets from individual experiments was normalized by comparing the bacterial load of each individual mice within a group to the median of the control group i.e. each data point represents the difference (Log 10 CFU control median-Log 10CFU vaccine group) between the control median CFU and the CFU of each individual animal (FIG. 6). In FIG. 6A comparison of the pooled data set for protection for the antigens latency associated antigens Rv0569, Rv2031c and the early antigens Ag85B, ESAT6, Rv3871, Rv3905 and Rv3445 of which the two latter are ESAT6 family proteins show that ESAT6 vaccinated animals are significantly better protected against reactivation compared to other antigens evaluated. Furthermore, protective levels attained following post-exposure vaccination with Rv3871, an ESX-1 protein also seem to be elevated compared to the other antigens (FIG. 6A). To further demonstrate the activity of ESAT6 in particular we compared the protection conferred by ESAT6 to the two fusion constructs H1 (Ag85B-ESAT6) and H56 (Ag85B-ESAT6-Rv2660) both of which contain ESAT6 (FIG. 6B). The analysis show that ESAT6 activity still result in protection against reactivation when included in the two above mentioned fusion constructs.

Example 7

Postexposure vaccination with another member of the ESX-1 family, Rv3871 seems to have an inhibitory effect on the reactivation process.

We evaluated other members of the ESX-1 family in parallel with ESAT6 and found that Rv3871 postexposure vaccination led to an induction of Rv3871 specific immune response (FIG. 7B) although not to the extent of the ESAT6 induced immune response (FIG. 7A). Nevertheless both ESAT6 and Rv3871 induced immune response were greater compared to saline control animals. The induction of vaccine specific immune response was associated with a lowered (median) bacterial load in both vaccine groups compared to the saline group. This indicated that Rv3871 may have a similar effect in protection against reactivation compared to ESAT6 demonstrated by the similar levels of bacterial numbers in these two groups compared to the somewhat elevated level in the control group (FIG. 7C)

REFERENCES

Andersen, P. 2007 15(1), 7-13
Anon. 2001. Global Tuberculosis Control. WHO Report.
Arend, S M., Infect Immun. 2000 68(6): 3314-3321.
Brodin, P. et al. Infect Immun. 2006, 74, 88-98
Cote-Sierra J, et al 1998, Gene October 9; 221(1):25-34
Doherty T M et al., 2002, J Clin Microbiol. February; 40(2): 704-6.
Gao L Y et al 2004, Molecular Microbiology 1677-93
Gosselin et al., 1992. J. Immunol. 149: 3477-3481
Guinn K I et al, 2004, Mol Microbiol. 51, 359-70
Guttstadt, A 1891. Die Wirksamkeit des Koch'schen Heilmittels gegen Tuberculosis, Polykliniken and Pathologisch/Anatomischen Institute der Preussischen Universitäten. Springer, Berlin.
Harboe, M., et al 1998 Infect. Immun. 66:2; 717-723
Hougardy et al 2007, PLoS ONE. October 3; 2(10):e926
Kilgus J et al, J Immunol. 1991 Jan. 1; 146(1):307-15
Leyten E M. Et al. Microbes Infect. 2006 8(8):2052-60.
Lin M Y and Ottenhoff T H, Biol. Chem. 2008, 389 (5): 497-511
Lowrie, D. B. et al 1999, Nature 400: 269-71
Lustig et al 1976, Cell Immunol 24(1):164-7
MacGurn J A et al. Mol Microbiol. 2005, 57:1653-63
Merrifield, R. B. Fed. Proc. Am. Soc. Ex. Biol. 21: 412, 1962 and J. Am. Chem. Soc. 85: 2149, 1963
Mowat et al 1991, Immunology 72(3):317-22
Mustafa, A S et al. 2000, Clin. Infect. Dis. 30 (suppl. 3) S201-S205
Nagai et al 1991, Infect. Immun 59:1; 372-382
Olsen A W et al, Eur J Immunol. 2000 June; 30(6):1724-32
Pym A S et al Nat Med 2003, 9, 533-9;
Pearson, W R. et al. 1988. Proc Natl Acad Sci USA, 85, 2444-2448.
Raghavan, S. et al. 2008, Nature 454, 717-721
Ravn, P. et al 1999. J. Infect. Dis. 179:637-645
Rolph, M S, and I. A. Ramshaw. 1997. Curr. Opin. Immunol. 9:517-24
Rogerson, B J et al Immunology 2006, 118, 195-201
Rosenkrands, I., et al 1998, Infect. Immun 66:6; 2728-2735
Ruhwald M. et al 2008 PLoS ONE. August 6; 3(8):e2858
Sambrook et al Molecular Cloning; A laboratory manual, Cold Spring Harbor Laboratories, NY, 1989
Seder, Nat. Rew. Immunol. 2008; 8(4):247-58
Sinigaglia F et al. Nature 1988 Dec. 22-29; 336(6201):778-80
Skjøt, R L V., et al 2000, Infect. Immun 68:1; 214-220
Smith J. et al. 2008, Infect Immun 76, 5478-87
Stanley, S A et al. 2003 Proc Natl Acad. Sci USA 100:12420-5
Stryhn, A., et al 1996 Eur. J. Immunol. 26:1911-1918
Turner, O C et al 2000 Infect Immun. 68:6:3674-9.
Talaat A M et al. 2007, J of Bact 189, 4265-74
Thompson J., et al Nucleic Acids Res 1994 22:4673-4680
Ulmer J. B et al 1993, Curr. Opin. Invest. Drugs 2(9): 983-989
van Pinxteren L A et al. 2000. Eur. J. Immunol. 30: 3689-98.

The invention claimed is:

1. A vaccine comprising an *M. tuberculosis* antigen polypeptide, which is constitutively expressed during infection with *M. tuberculosis* or a nucleic acid encoding said *M. tuberculosis* antigen polypeptide, wherein said vaccine prevents reactivation of tuberculosis in latently infected individuals, wherein the vaccine further comprises an adjuvant comprising IC31 or DDA/TDB, with or without poly I:C, and wherein the *M. tuberculosis* antigen polypeptide, which is constitutively expressed, belongs to the ESX-1 secretion system and comprises:
   i) a first polypeptide sequence set forth in any one of SEQ ID NO. 3, 4, 5, 6, 7, 8, 9, 14, 15, 16, 17, 18, 32, 33, or 34; or
   ii) a second polypeptide sequence that comprises at least 80% sequence identity to any one of the sequences in (i), wherein said second polypeptide sequence is immunogenic.

2. The vaccine according to claim 1, wherein said *M. tuberculosis* antigen polypeptide comprises the polypeptide sequence set forth in SEQ ID NO. 3, 4, 5, 6, 7, 8, 9, 14, 15, 16, 17, 18, 32, 33 or 34.

3. The vaccine according to claim 1, wherein the *M. tuberculosis* antigen polypeptide comprises the polypeptide sequence selected from the group consisting of SEQ ID NO. 19, 20, 21, 22, 23, 24, 25, 26, 27, 28, 29, 30 and 31.

4. The vaccine according to claim 1, wherein the *M. tuberculosis* antigen polypeptide is fused to an additional antigen polypeptide, which is expressed by bacteria within the mycobacteria family, so as to form a fusion polypeptide.

5. The vaccine according to claim 4, wherein the fusion polypeptide is constitutively expressed.

6. The vaccine according to claim 5, wherein the fusion polypeptide comprises ESAT6 fused to CFP10.

7. The vaccine according to claim 1, further comprising a live recombinant vaccine against *M. tuberculosis*, a DNA vaccine against *M. tuberculosis*, a protein vaccine against *M. tuberculosis*, or an adjuvant.

8. The vaccine according to claim 7, wherein the adjuvant comprises DDA/TDB with or without poly I:C.

9. The vaccine according to claim 1, wherein the *M. tuberculosis* antigen polypeptide is lipidated.

10. A method for treating or inhibiting latent tuberculosis in an animal, including a human being, comprising administering the vaccine of claim 1 to an animal in need thereof.

11. A method for treating an animal, including a human being, against reactivation of the tuberculosis infection caused by a virulent mycobacteria, comprising administering to the animal the vaccine according to claim 1.

12. The method according to claim 11, wherein said vaccine is administered during latent stage infection.

13. A method for treating or inhibiting an animal, including a human being, against reactivation of a latent infection caused by a species of *Mycobacterium tuberculosis, M. Bovis* or *M. africanum* comprising administering to the animal the vaccine according to claim 1.

14. The method according to claim 13, wherein said vaccine is administered during latent stage infection.

15. The method according to claim 13, wherein said vaccine comprises any one of the polypeptide sequences set forth in SEQ ID NO. 3, 4, 5, 6, 7, 8, 9, 14, 15, 16, 17, 18, 32, 33 or 34.

16. The vaccine according to claim 1, wherein said second polypeptide sequence comprises at least 85% sequence identity to any one of the sequences in (i).

17. The vaccine according to claim 1, wherein said second polypeptide sequence comprises at least 90% sequence identity to any one of the sequences in (i).

18. The vaccine according to claim 1, wherein said second polypeptide sequence comprises at least 93% sequence identity to any one of the sequences in (i).

19. The vaccine according to claim 1, wherein said second polypeptide sequence comprises at least 95% sequence identity to any one of the sequences in (i).

20. The vaccine according to claim 1, wherein said second polypeptide sequence comprises at least 97% sequence identity to any one of the sequences in (i).

* * * * *